(12) United States Patent
Haneda et al.

(10) Patent No.: US 12,180,450 B2
(45) Date of Patent: *Dec. 31, 2024

(54) SCAFFOLDING MATERIAL FOR STEM CELL CULTURES AND STEM CELL CULTURE METHOD USING SAME

(71) Applicant: SEKISUI CHEMICAL CO., LTD., Osaka (JP)

(72) Inventors: Satoshi Haneda, Osaka (JP); Yuriko Manabe, Osaka (JP); Ryoma Ishii, Osaka (JP); Hiroki Iguchi, Osaka (JP); Hiroshi Yamauchi, Osaka (JP); Takahiro Omura, Saitama (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 500 days.

This patent is subject to a terminal disclaimer.

(21) Appl. No.: 16/958,204

(22) PCT Filed: Dec. 27, 2018

(86) PCT No.: PCT/JP2018/048386
§ 371 (c)(1),
(2) Date: Jun. 26, 2020

(87) PCT Pub. No.: WO2019/131978
PCT Pub. Date: Jul. 4, 2019

(65) Prior Publication Data
US 2020/0362289 A1 Nov. 19, 2020

(30) Foreign Application Priority Data
Dec. 27, 2017 (JP) .................. 2017-252420

(51) Int. Cl.
| | | |
|---|---|---|
| C12M 1/12 | (2006.01) | |
| C08F 124/00 | (2006.01) | |
| C08L 79/02 | (2006.01) | |
| C12M 3/00 | (2006.01) | |
| C12N 5/00 | (2006.01) | |
| C12N 5/0735 | (2010.01) | |
| C12N 5/074 | (2010.01) | |

(52) U.S. Cl.
CPC ........... *C12M 25/14* (2013.01); *C08F 124/00* (2013.01); *C08L 79/02* (2013.01); *C12M 21/06* (2013.01); *C12N 5/0068* (2013.01); *C12N 5/0606* (2013.01); *C12N 5/0607* (2013.01); *C12N 5/0696* (2013.01); *C08L 2666/36* (2013.01); *C12N 2533/30* (2013.01); *C12N 2533/70* (2013.01)

(58) Field of Classification Search
CPC ...... C12M 25/14; C12M 21/06; C08F 124/00; C08L 79/02; C08L 2666/36; C12N 5/0068; C12N 5/0606; C12N 5/0607; C12N 5/0696; C12N 2533/30; C12N 2533/70

USPC ......................................................... 435/395
See application file for complete search history.

(56) References Cited

U.S. PATENT DOCUMENTS

| | | |
|---|---|---|
| 4,537,790 A | 8/1985 | Horodniceanu et al. |
| 5,393,668 A | 2/1995 | Cinatl et al. |
| 5,880,216 A | 3/1999 | Tanihara et al. |
| 6,984,692 B2 | 1/2006 | Kumaki et al. |
| 8,153,715 B2 | 4/2012 | Stark |
| 2002/0161440 A1 | 10/2002 | Son et al. |
| 2005/0164377 A1 | 7/2005 | Miyabayashi et al. |
| 2006/0235084 A1 | 10/2006 | Heller et al. |
| 2007/0122901 A1 | 5/2007 | Morita et al. |
| 2009/0130756 A1 | 5/2009 | Klann et al. |
| 2009/0176937 A1 | 7/2009 | Frank et al. |
| 2011/0129924 A1 | 6/2011 | Ying et al. |
| 2011/0318829 A1 | 12/2011 | Tazaki et al. |
| 2012/0015177 A1 | 1/2012 | Kim |
| 2012/0202070 A1 | 8/2012 | Asanuma et al. |
| 2013/0280725 A1 | 10/2013 | Ismagilov et al. |
| 2013/0309679 A1 | 11/2013 | Ismagilov et al. |
| 2014/0210338 A1 | 7/2014 | Matsumura et al. |
| 2014/0315235 A1 | 10/2014 | Puschmann et al. |
| 2015/0010919 A1 | 1/2015 | Feinberg et al. |
| 2015/0140652 A1 | 5/2015 | Sasai et al. |
| 2018/0126713 A1 | 5/2018 | Glaser et al. |

(Continued)

FOREIGN PATENT DOCUMENTS

| | | |
|---|---|---|
| CN | 1216581 | 5/1999 |
| CN | 101528822 | 9/2009 |

(Continued)

OTHER PUBLICATIONS

Extended European Search Report issued Dec. 23, 2021 in corresponding European Patent Application No. 18893713.0, 7 pages.
Office Action issued Sep. 21, 2022 in U.S. Appl. No. 16/958,218, 15 pages.
Extended European Search Report issued Oct. 12, 2021 in corresponding European Patent Application No. 18893580.3, 8 pages.
Office Action dated Mar. 31, 2022 in corresponding U.S. Appl. No. 16/958,218, filed Jun. 26, 2020, 19 pages.
Translation of the International Preliminary Report on Patentability issued Jul. 2, 2020 in International (PCT) Application No. PCT/JP2018/048386.

(Continued)

*Primary Examiner* — Jennifer M. H. Tichy
(74) *Attorney, Agent, or Firm* — Wenderoth, Lind & Ponack, L.L.P.

(57) ABSTRACT

A scaffolding material for stem cell culture, which has a dispersion component $\gamma^d$ of the surface free energy of 24.5 or more and less than 45.0, and a dipole component $\gamma^p$ of the surface free energy of 1 or more and less than 20.0. According to the scaffolding material for stem cell culture, the scaffolding material can have suitable hydrophilicity and strength, high fixation of stem cells after seeding, and highly efficient cell proliferation.

19 Claims, 9 Drawing Sheets

(56) References Cited

U.S. PATENT DOCUMENTS

| | | |
|---|---|---|
| 2018/0194935 A1 | 7/2018 | Maeda et al. |
| 2019/0106561 A1 | 4/2019 | Ukidwe |
| 2020/0362289 A1 | 11/2020 | Haneda et al. |
| 2020/0399576 A1 | 12/2020 | Haneda et al. |
| 2021/0071147 A1 | 3/2021 | Haneda et al. |

FOREIGN PATENT DOCUMENTS

| | | | |
|---|---|---|---|
| CN | 104428651 | | 3/2015 |
| CN | 107406652 | | 11/2017 |
| EP | 0339371 | | 11/1989 |
| EP | 0 897 000 | | 2/1999 |
| EP | 2 385 105 | | 11/2011 |
| EP | 2 821 789 | | 1/2015 |
| EP | 3 733 834 | | 11/2020 |
| EP | 4 286 508 | | 12/2023 |
| JP | 6-153905 | | 6/1994 |
| JP | 9-131397 | | 5/1997 |
| JP | 10-52268 | | 2/1998 |
| JP | H10204204 | * | 8/1998 |
| JP | 2001-89574 | | 4/2001 |
| JP | 2006-42758 | | 2/2006 |
| JP | 2006-272002 | | 10/2006 |
| JP | 2006-314285 | | 11/2006 |
| JP | 2009-39138 | | 2/2009 |
| JP | 2009-273444 | | 11/2009 |
| JP | 2010-91689 | | 4/2010 |
| JP | 2010-158180 | | 7/2010 |
| JP | 2010-168444 | | 8/2010 |
| JP | 4956753 | | 6/2012 |
| JP | 2015-142525 | | 8/2015 |
| JP | 2015-195752 | | 11/2015 |
| JP | 2015-199932 | | 11/2015 |
| JP | 2015-205462 | | 11/2015 |
| JP | 2016-186044 | | 10/2016 |
| JP | 2017-23008 | | 2/2017 |
| JP | 2017-46676 | | 3/2017 |
| JP | 6144437 | | 6/2017 |
| JP | 2017-163898 | | 9/2017 |
| JP | 6427450 | | 11/2018 |
| KR | 2007-0122519 | | 12/2007 |
| TW | 201540829 | | 11/2015 |
| WO | 97/41216 | | 11/1997 |
| WO | 01/05877 | | 1/2001 |
| WO | 2006/093207 | | 9/2006 |
| WO | 2012/023518 | | 2/2012 |
| WO | 2013/183777 | | 12/2013 |
| WO | 2015/129837 | | 9/2015 |
| WO | 2016/122123 | | 8/2016 |
| WO | 2017/057663 | | 4/2017 |

OTHER PUBLICATIONS

Translation of the International Preliminary Report on Patentability issued Jul. 9, 2020 in International (PCT) Application No. PCT/JP2018/048389.
Translation of the International Preliminary Report on Patentability issued Jul. 9, 2020 in International (PCT) Application No. PCT/JP2018/048391.
International Search Report issued Mar. 26, 2019 in International (PCT) Application No. PCT/JP2018/048386.
Bayramoglu et al., "Preparation and Characterization of Poly(hydroxyethyl methacry late-co-poly(ethyl-eneglycol-methacrylate)/Hydroxypropyl-chitosan) Hydrogel Films: Adhesion of Rat Mesenchymal Stem Cell," Macromolecular Research, 2011, vol. 19, No. 4, pp. 385-395.
Rebollar et al., "Physicochemical modifications accompanying UV laser induced surface structures on poly(ethyleneterephthalate) and their effect on adhesion of mesenchymal cell," Phys. Chem. Chem. Phys., 2014, vol. 16, pp. 17551-17559.
Togami et al., "Effects of water holding capability of the PVF sponge on the adhesion and differentiation of rat bone marrow stem cell culture," Society For Biomaterials, 2013, vol. 102A, No. 1, pp. 247-253.
Saha et al., "Surface-engineered substrates for improved human pluripotent stem cell culture under fully defined conditions," PNAS, 2011, vol. 108, No. 46, pp. 18714-18719.
Tunma et al., "Improving the attachment and proliferation of umbilical cord mesenchymal stem cells on modified polystyrene by nitrogen-containing plasma," Cytotechnology, 2013, vol. 65, pp. 119-134.
Togami et al., "Effects of the water-holding capability of polyvinyl formal sponges on osteogenic ability in in vivo experiments," Society For Biomaterials, 2014, vol. 103B Issue 1, pp. 188-194.
Miyoshi et al., "Three-dimensional culture of mouse bone marrow cells within a porous polymer scaffold: effects of oxygen concentration and stromal layer on expansion of haematopoietic progenitor cells," Journal of Tissue Engineering and Regenerative Medicine, 2011, vol. 5, pp. 112-118.
Notice of Ground of Rejection mailed on Apr. 14, 2020 in Japanese Patent Application No. 2019-562491 with English-language translation.
Extended European Search Report issued Oct. 8, 2021 in corresponding European Patent Application No. 18897018.0, 8 pages.
First Examination Report issued Jun. 14, 2022 in corresponding Indian Patent Application No. 202047029411, 7 pages.
Office Action issued Apr. 12, 2023 in U.S. Appl. No. 16/958,218, 18 pages.
Office Action issued Jan. 26, 2023 in U.S. Appl. No. 16/958,182, 28 pages.
Poly(vinylamine), Polymer source, Inc., downloaded on Jan. 19, 2023 from www.polymersource.ca/index.php?route=product, one page (Year: 2023).
Office Action issued Jun. 27, 2023 in U.S. Appl. No. 16/958,182, 18 pages.
Lee et al., "Cell Behavior On Polymer Surfaces With Different Functional Groups", Science and Technology of Polymers and Advanced Materials, Edited by P.N. Prasad et al., Plenum Press, New York, p. 535-545 (Year: 1998), 11 pages.
Office Action issued Jul. 12, 2023 in U.S. Appl. No. 16/919,312, 28 pages.
Office Action issued Jun. 22, 2023 in U.S. Appl. No. 16/919,452, 13 pages.
Office Action issued Feb. 10, 2023 in U.S. Appl. No. 16/919,452, 23 pages.
Office Action issued Nov. 21, 2023 in corresponding U.S. Appl. No. 16/919,452.
Meng Zhong Wang, "Handbook of Adhesive Application", p. 16-20, Chemical Industry Press, publication date: Nov. 30, 1987.
Office Action issued Oct. 13, 2023 in related U.S. Appl. No. 16/958,218, 16 pages.
Examination report No. 1 issued Nov. 1, 2023 in corresponding Australian Patent Application No. 2018398052, 4 pages.
Examination report No. 1 issued Nov. 16, 2023 in corresponding Australian Patent Application No. 2018398050, 3 pages.
Official Communication dated Sep. 18, 2023 issued in corresponding Indian Patent Application No. 202047029416, 2 pages.
Extended European Search Report issued Jan. 31, 2024 in corresponding European Patent Application No. 23203425.6.
Office Action issued Mar. 4, 2024 in corresponding U.S. Appl. No. 16/919,312.
Office Action issued May 8, 2024 in related U.S. Appl. No. 16/958,218, 20 pages.
Wang Mengzhong, et al."Handbook of Adhesion Application", Chemical Industry Press, Dec. 12, 2023, pp. 1-6.
Chen Huipeng (ed.), "Advances in Pharmaceutical Bioengineering", People's Military Medical Press, Jul. 2004, p. 259, with English-language translation.
Wang Yingjun (ed), "Biomedical Ceramic Materials", South China University of Technology Press, Oct. 2010, pp. 167-168, with English-language translation.
Office Action issued Oct. 4, 2024 in U.S. Appl. No. 16/958,218.

* cited by examiner

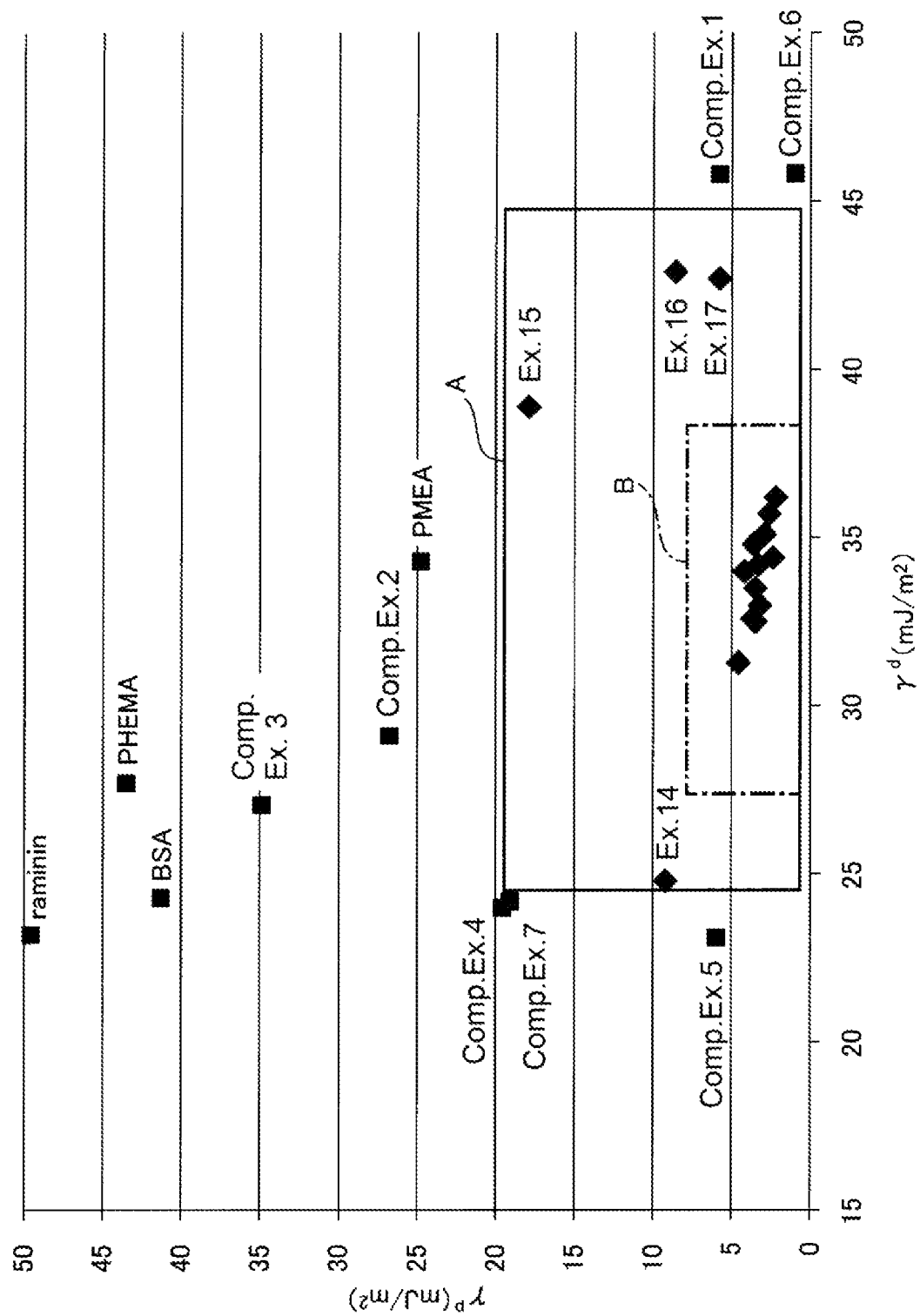

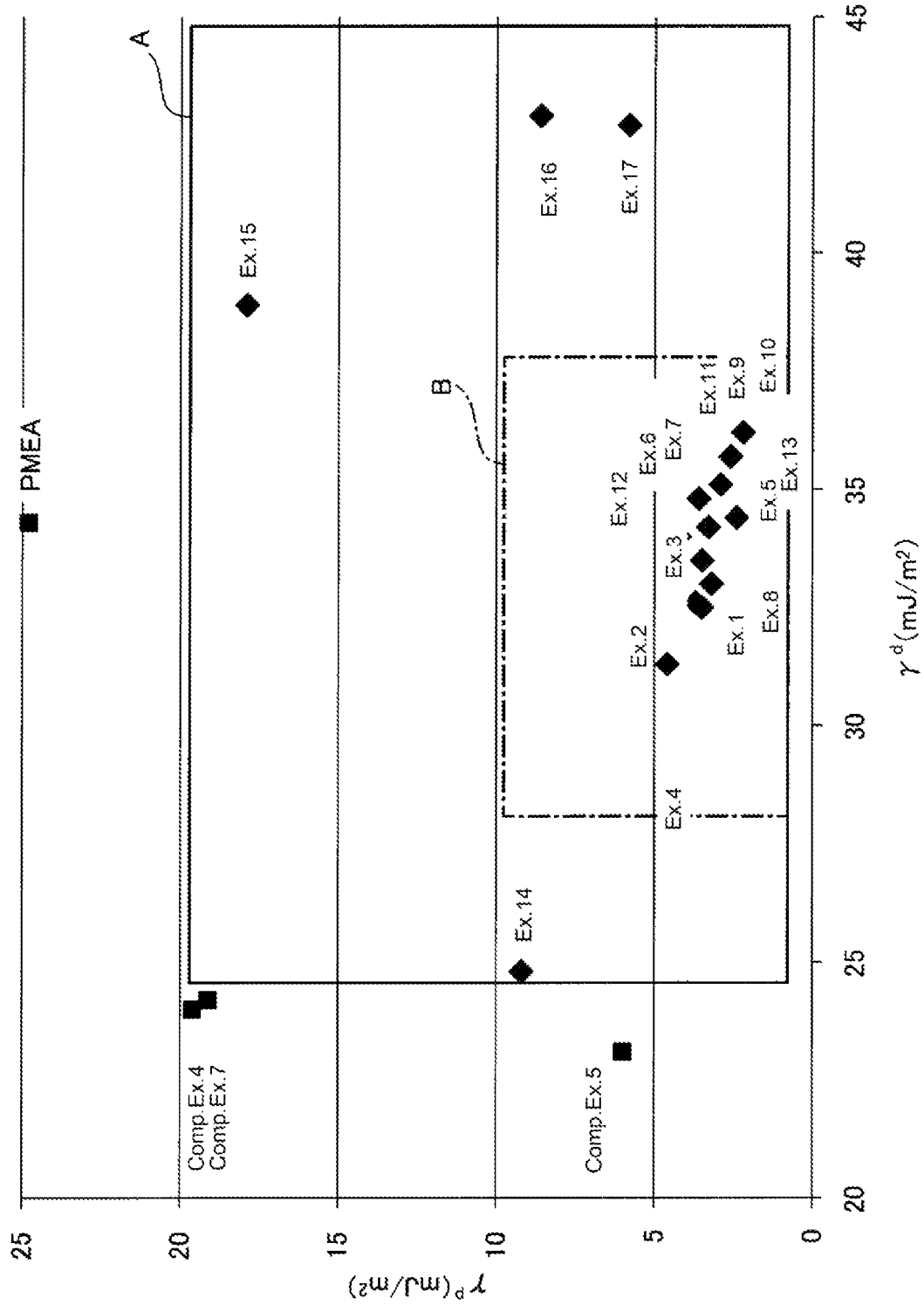

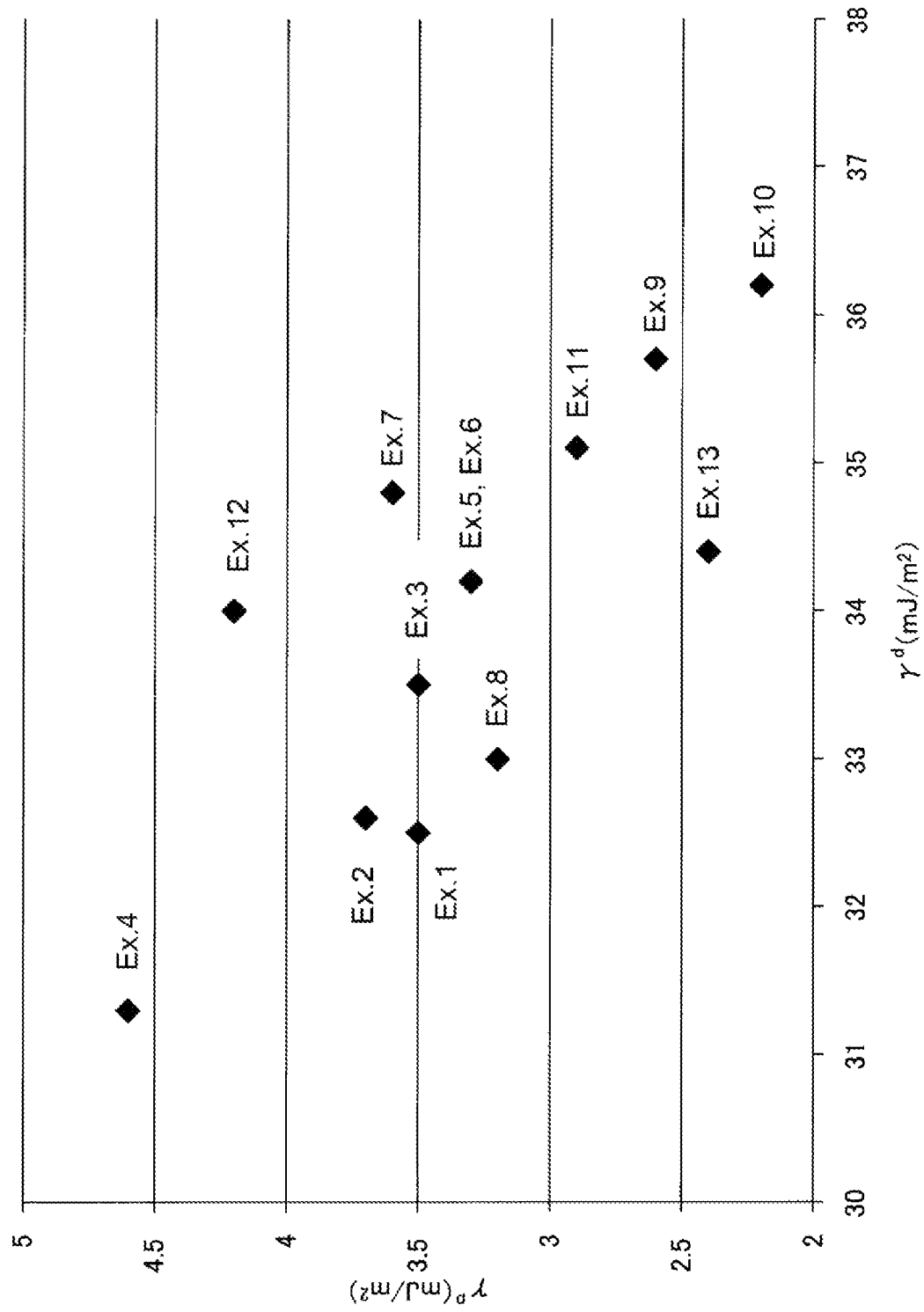

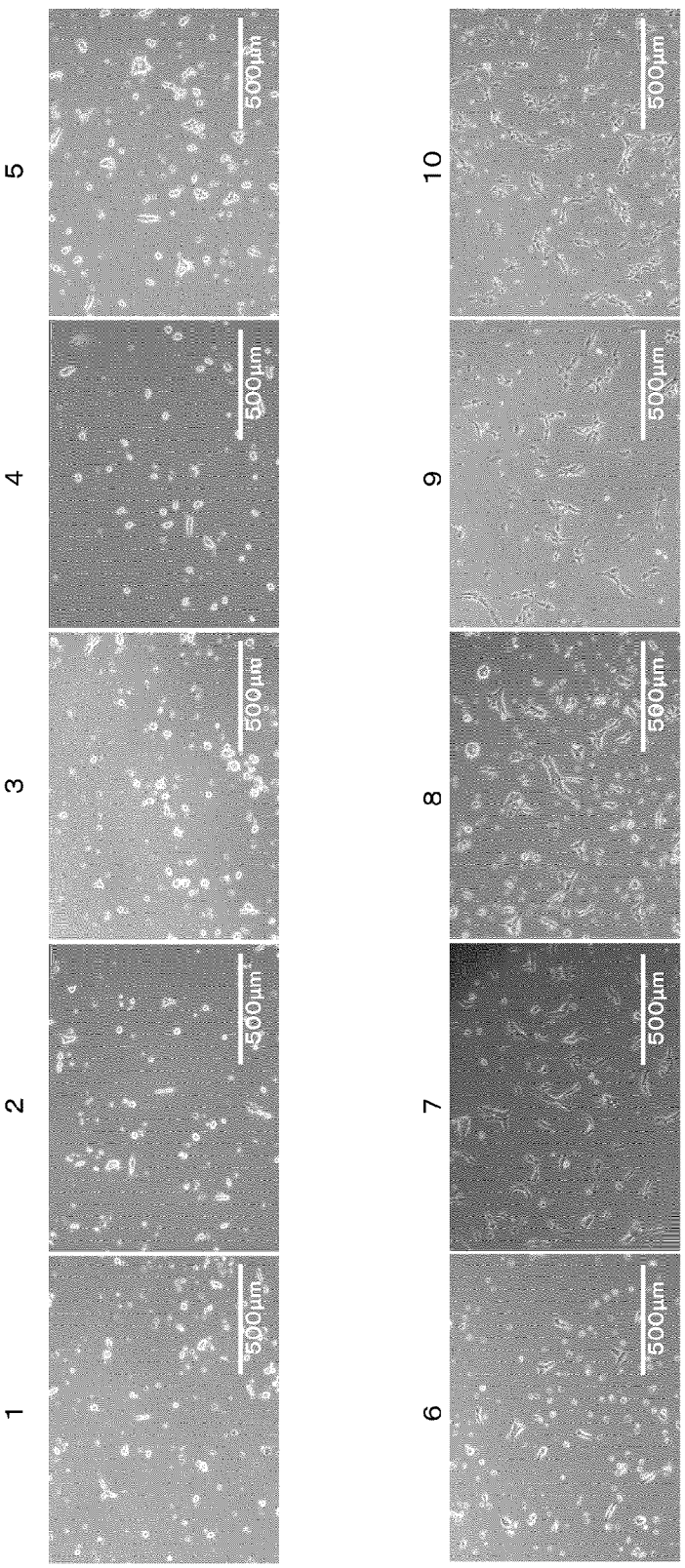
[FIG. 4]

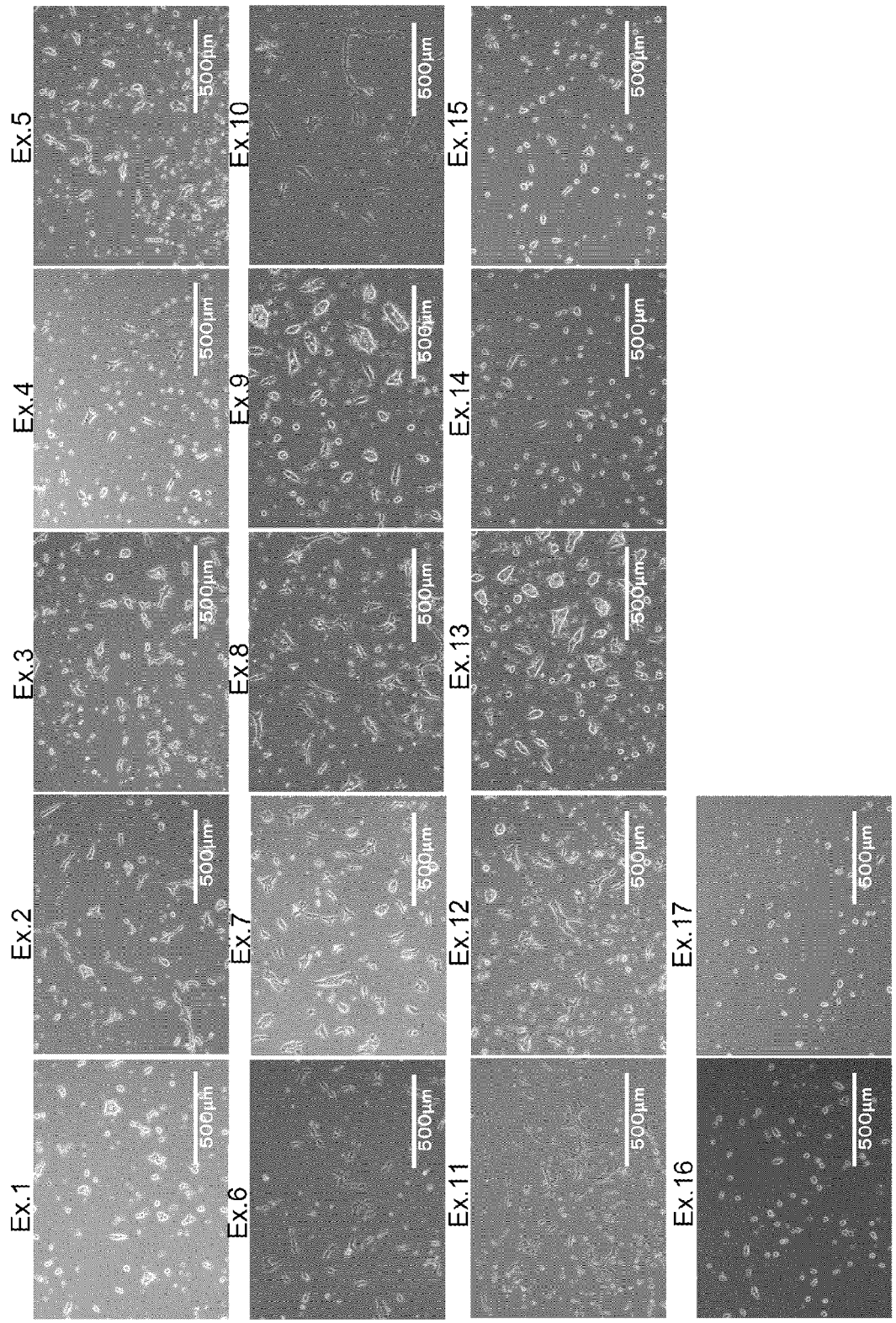

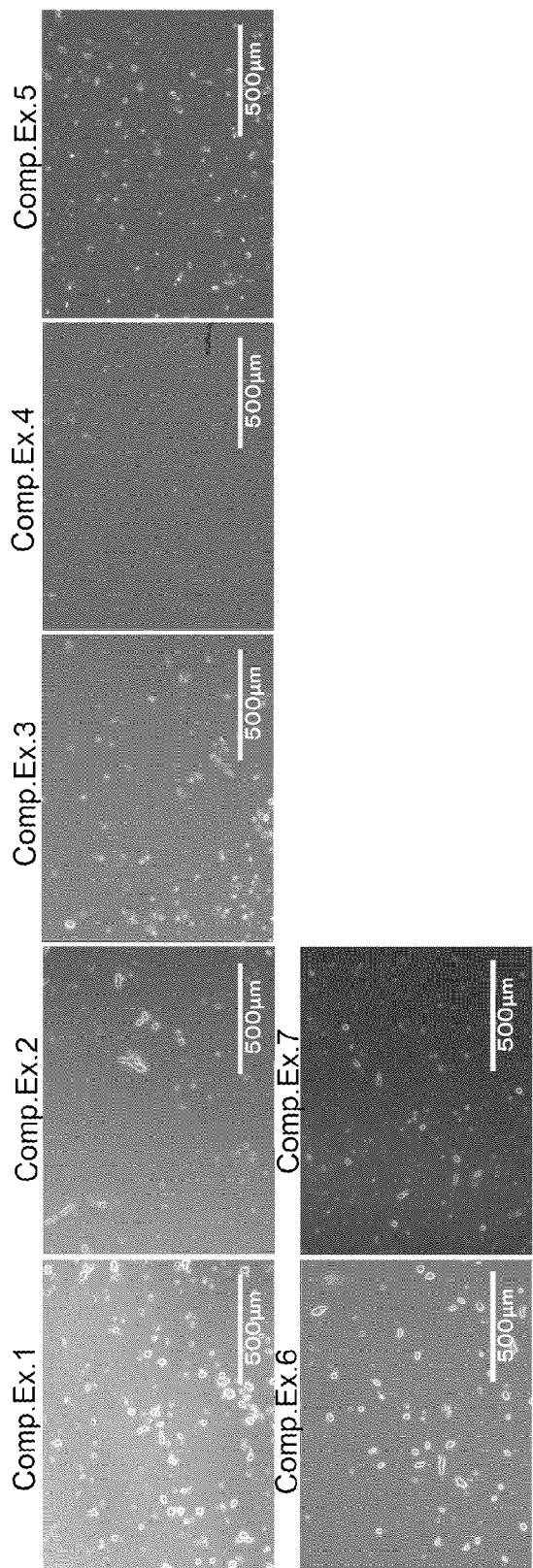
[FIG. 6]

[FIG. 7]
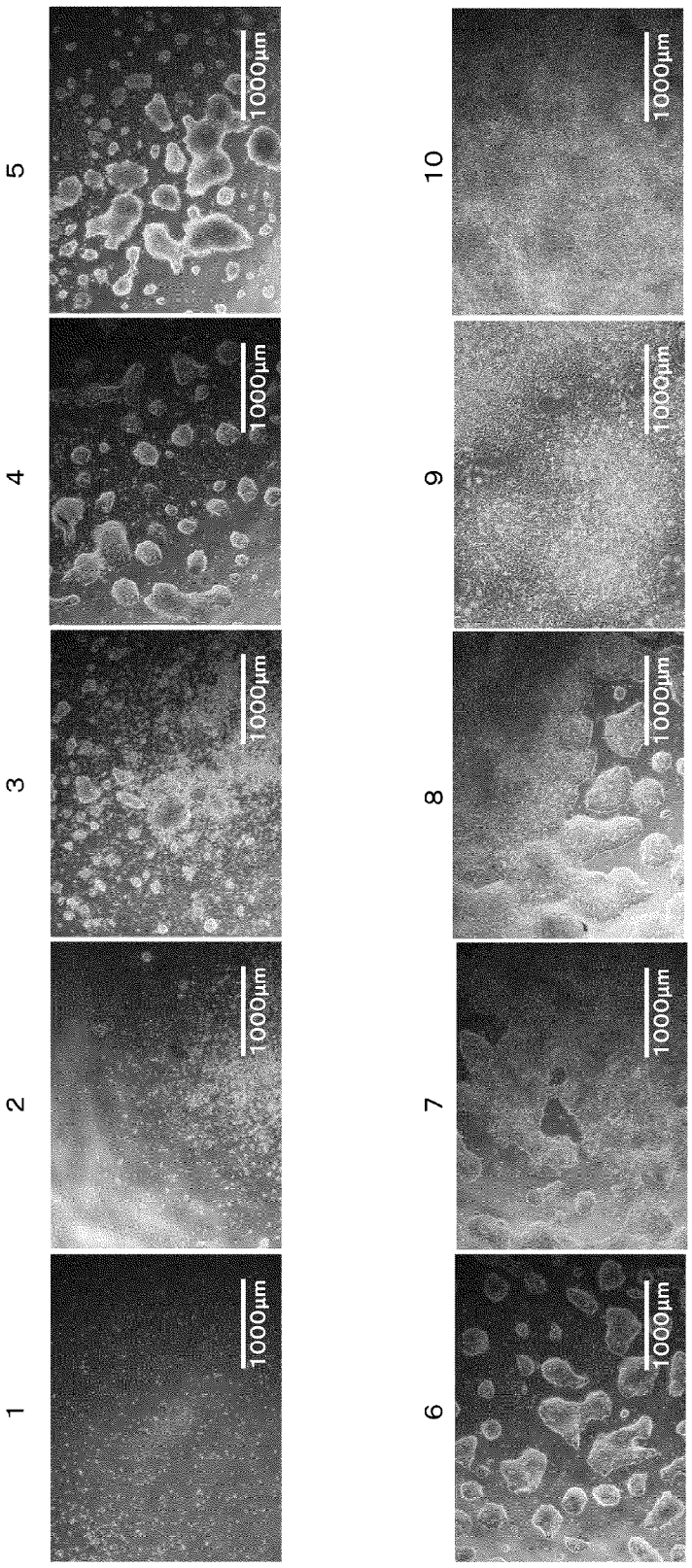

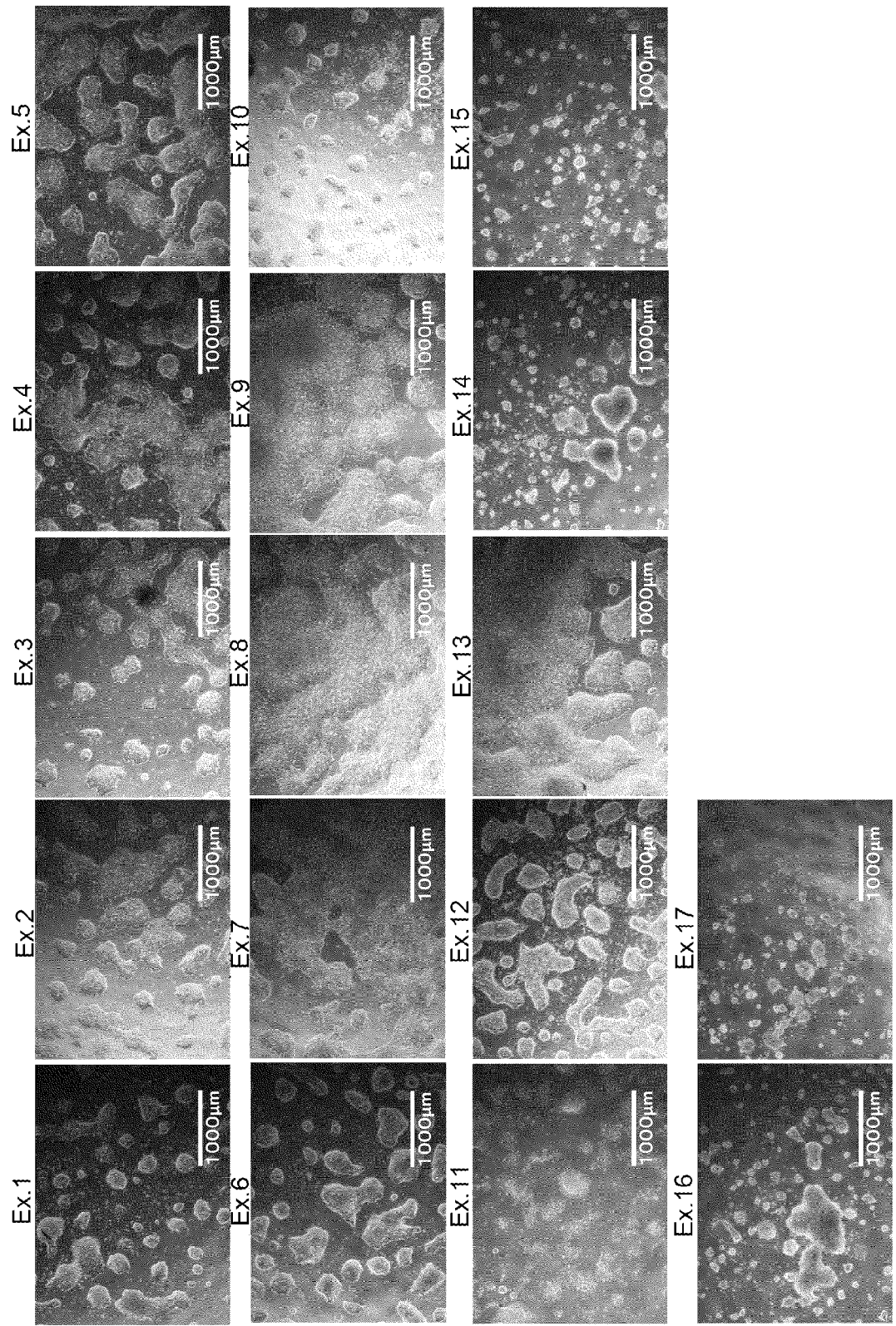
[FIG. 8]

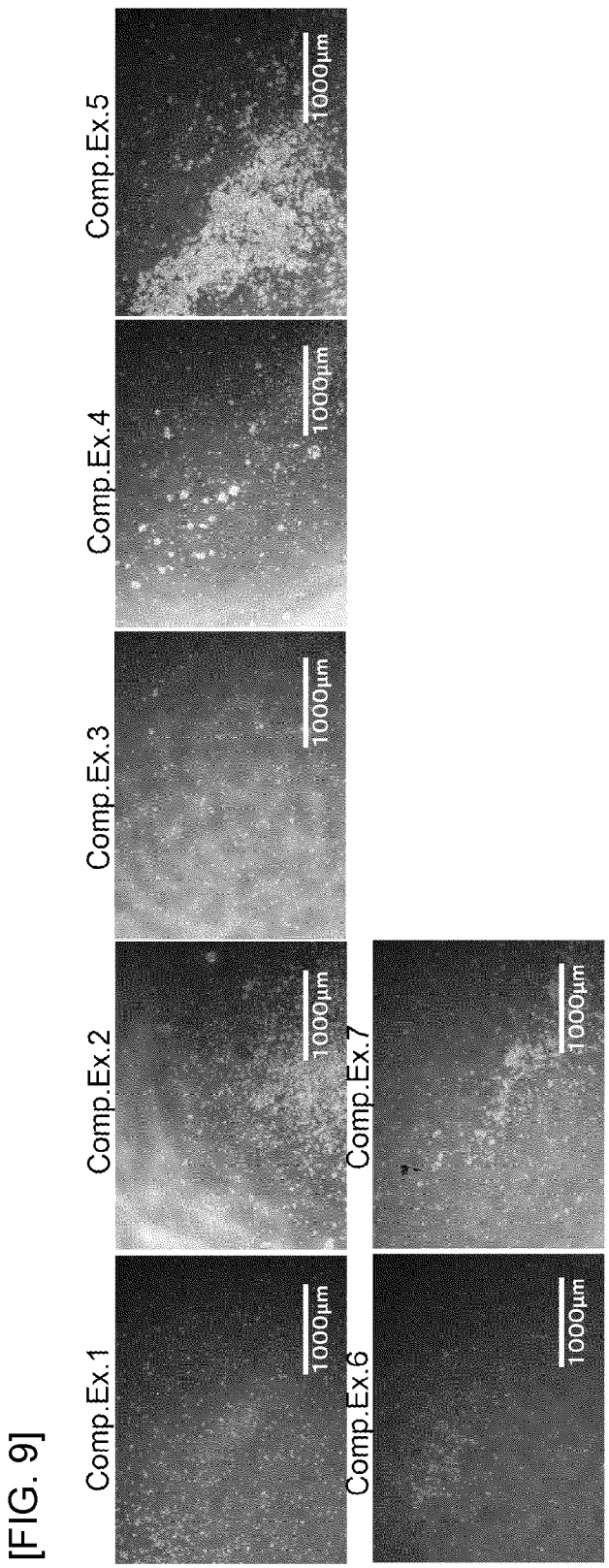
[FIG. 9]

SCAFFOLDING MATERIAL FOR STEM CELL CULTURES AND STEM CELL CULTURE METHOD USING SAME

TECHNICAL FIELD

The present invention relates to a scaffolding material for stem cell culture and a stem cell culture method using the same.

BACKGROUND ART

Stem cells are expected to be applied on drug discovery and regenerative medicine. Stem cells are cells that have self-renew potency and differentiation potency, including pluripotent stem cells that can differentiate into all cell types, and tissue stem cells and tissue progenitor cells that can differentiate only into constituent cell types of the body tissue in the same series. Examples of the pluripotent stem cells include human pluripotent stem cells (hPSCs) such as human embryonic stem cells (hESCs) and human induced pluripotent stem cells (hiPSCs). It is an essential basic technology to cultivate and proliferate stem cells safely and with good reproducibility for medical application of these cells. In particular, for industrial application on regenerative medicine, it is necessary to handle a large amount of stem cells in an undifferentiated state. Accordingly, extensive studies have been conducted on techniques for proliferating stem cells using natural and synthetic macromolecules and feeder cells, and maintaining the pluripotency (or multipotency). In particular, it is known that cell fixation after seeding is extremely high when an adhesive protein such as laminin or vitronectin, or a matrigel derived from mouse sarcoma is used as a natural polymer.

However, there are problems in that natural polymers are expensive because of their very low productivity, variations between lots can be seen because they are naturally occurring substances, and there are safety concerns due to animal-derived components.

In order to solve the above problems, a stem cell culture resin carrier using a synthetic resin has been proposed. For example, the column of Examples in Patent Document 1 discloses a polyvinyl acetal compound having a degree of acetalization of 20 to 60 mol % in order to provide a scaffold having excellent hydrophilicity and water resistance in culturing mouse fibroblasts. The column of Examples in Patent Document 2 discloses a hydrogel composed of an acrylic polymer in culturing mouse ES cells. The column of Examples in Patent Document 3 discloses a hydrophilic and flexible polyrotaxane gel in culturing mouse IPS dells.

RELATED ART DOCUMENT

Patent Document

Patent Document 1: JP 2006-314285 A
Patent Document 2: JP 2010-158180 A
Patent Document 3: JP 2017-23008 A

SUMMARY OF THE INVENTION

Problems to be Solved by the Invention

However, Patent Document 1 has a problem in that the scaffolding material resin is swelled in a medium due to its high hydrophilicity, and thus is peeled off. In addition, there is a problem in that the fixation of stem cells or pluripotent stem cells after seeding is so low that the cells do not proliferate sufficiently. In Patent Document 2, sodium 2-acrylamide-2-methylpropane sulfonate, sodium p-styrene sulfonate and N,N'-dimethylacrylamide are used, so that there is a problem in that the scaffolding material resin is swelled in a medium due to its high hydrophilicity, and thus is peeled off. Patent Document 3 has a problem in that the scaffolding material resin is swelled in a medium due to its high hydrophilicity, and thus is peeled off. In addition, there is a problem in that the scaffolding material is so flexible that differentiation into cardiomyocytes is promoted.

As described above, there have been needs of a scaffolding material for stem cell culture having suitable hydrophilicity and strength, and a stem cell culture method using the same.

An object of the present invention is to provide a scaffolding material for stem cell culture having suitable hydrophilicity and strength, high fixation of stem cells after seeding, and highly efficient cell proliferation, and a stem cell culture method using the same.

Means for Solving the Problems

The present invention relates to the followings.

(1) A scaffolding material for culturing a stem cell, having a dispersion component $\gamma^d$ of the surface free energy of 24.5 or more and less than 45.0, and a dipole component $\gamma^p$ of the surface free energy of 1.0 or more and less than 20.0.

(2) The scaffolding material for culturing a stem cell according to (1), containing a synthetic resin.

(3) The scaffolding material for culturing a stem cell according to (2), in which the synthetic resin contains at least any one of a polyvinyl acetal skeleton and a poly(meth) acrylic ester skeleton.

(4) The scaffolding material for culturing a stem cell according to (2), in which the synthetic resin is a polyvinyl acetal resin.

(5) A scaffolding material for culturing a stem cell containing a synthetic resin, the synthetic resin containing a polyvinyl acetal resin, and the degree of acetalization of the polyvinyl acetal resin being higher than 60 mol %.

(6) The scaffolding material for culturing a stem cell according to (4) or (5), in which the polyvinyl acetal resin contains at least one selected from the group consisting of a structural unit having an imine structure, a structural unit having an amino group and a structural unit having an amide structure.

(7) The scaffolding material for culturing a stem cell according to (6), in which the polyvinyl acetal resin has a total content of the structural unit having an imine structure, the structural unit having an amino group and the structural unit having an amide structure of 0.1 mol % or more and 20 mol % or less.

(8) The scaffolding material for culturing a stem cell according to any one of (1) to (7), in which the stem cell is a pluripotent stem cell.

(9) A container for culturing a stem cell, including a resin film made of the scaffolding material for culturing a stem cell according to any one of (1) to (8) on at least a part of a cell culture region.

(10) A fiber for culturing a stem cell, including the scaffolding material for culturing a stem cell according to any one of (1) to (8).

(11) A method for culturing a stem cell, using the scaffolding material according to any one of (1) to (8).

(12) The method for culturing a stem cell according to (11), including a step of seeding a ell mass on the scaffolding material.

Effect of the Invention

According to the present invention, there are provided a scaffolding material for stem cell culture having suitable hydrophilicity and strength, and high fixation of stem cells after seeding, and a stem cell culture method using the same.

BRIEF DESCRIPTION OF DRAWINGS

FIG. 1 is a view summarizing the relationship of $\gamma^p$ to $\gamma^d$ of main synthetic resins.
FIG. 2 is a partially enlarged view of FIG. 1.
FIG. 3 is a partially enlarged view of FIG. 1.
FIG. 4 is a view showing evaluation criteria for initial adhesion 24 hours after cell seeding.
FIG. 5 is phase contrast micrographs in the scaffolding materials for stem cell culture according to Examples 24 hours after cell seeding.
FIG. 6 is phase contrast micrographs in the scaffolding material for stem cell culture according to Comparative Examples 24 hours after cell seeding.
FIG. 7 is a view showing evaluation criteria for cell proliferation 5 days after cell seeding.
FIG. 8 shows phase contrast micrographs in the scaffolding materials for stem cell culture according to Examples 5 days after cell seeding.
FIG. 9 shows phase contrast micrographs in the scaffolding material for stem cell culture according to Comparative Examples 5 days after cell seeding.

MODES FOR CARRYING OUT THE INVENTION

Hereinafter, a description is made of the present invention with reference to embodiments, but the present invention is not limited to the following embodiments.

First, a description is made of the terms used in this specification.

"Stem cell" refers to a cell having self-renew potency and differentiation potency. Among the stem cells, those that have an ability to self-renew and differentiate from one cell into all cells of endoderm, mesoderm and ectoderm are referred to as "pluripotent stem cells".

Examples of the pluripotent stem cells include induced pluripotent stem cells (hereinafter referred to as "IPS cells"), embryonic stem cells (hereinafter referred to as "ES cells"), Muse cells (multilinege differentiating stress enduring cells), embryonic cancer cells, embryonic germ cells and mGS cells (multipotent germ stem cells).

Among the stem cells, those that have an ability to self-renew, belong to any of the ectodermal, endodermal, mesodermal and germline tissues, and exhibit a limited ability to differentiate into the constituent cell types of an organ to which they belong are referred to as "tissue stem cells" and "tissue progenitor cells."

Examples of the tissue stem cells and tissue progenitor cells include neural stem cells, neural crest stem cells, retinal stem cells, corneal stem cells, keratinocyte epidermal stem cells, melanocyte stem cells, mammary gland stem cells, liver stem cells, intestinal stem cells, respiratory tract stem cells, hematopoietic stem cells, mesenchymal stem cells, cardiac stem cells, vascular endothelial progenitor cells, vascular pericytes, skeletal muscle stem cells, adipose stem cells, renal progenitor cells and sperm stem cells. Such stem cells may include, for example, stem cells described "Understanding It Better! Stem Cells and Regenerative Medicine (Motto Yoku Wakaru! Kansaibo to Saisei Iryo)" (Yodosha Co., Ltd., Kenji Osafune).

Scaffolding Material for Stem Cell Culture 1

In order to solve the above problems, the present inventors have found that the above problems can be solved by controlling the surface free energy of a scaffolding material for stem cell culture, and thus have completed the present invention. In other words, a first aspect of the present invention relates to a scaffolding material for stem cell culture in which the dispersion component $\gamma^d$ and the dipole component $\gamma^p$ of the surface free energy are within a certain range.

Note that the dispersion component $\gamma^d$ and the dipole component $\gamma^p$ of the surface free energy in this specification can be measured using the Kaelble-Uy theoretical formula.

Here, the Kaelble-Uy theoretical formula is based on the assumption that the total surface free energy $\gamma$ is composed of the sum of the dispersion component $\gamma^d$ and the dipole component $\gamma^p$, as represented by equation (1).

[Equation 1]

$$\gamma = \gamma^d + \gamma^p \tag{1}$$

In addition, when the surface free energy of the liquid surface is represented by $\gamma_l$, the surface free energy of the solid is represented by $\gamma_s$, and the contact angle is represented by $\theta$, the following equation (2) is established.

[Equation 2]

$$\gamma_l(1+\cos\theta) = 2\sqrt{\gamma_s^d \gamma_l^d} + 2\sqrt{\gamma_s^p \gamma_l^p} \tag{2}$$

Accordingly, using two types of liquids (pure water and diiodomethane in the present invention) with known components of $\gamma_l$, the dispersion component $\gamma^d$ and the dipole component $\gamma^p$ of a scaffolding material for stem cell culture are determined by measuring each contact angle $\theta$ with respect to the scaffolding material for stem cell culture and solving simultaneous equations for $\gamma_s^d$ and $\gamma_s^p$.

The contact angle of pure water can be obtained by dropping 1 μL of pure water onto the scaffolding material and then photographing the droplet image after 30 seconds using a contact angle meter (manufactured by Kyowa Interface Science, Inc., DMo-701). In addition, the contact angle of diiodomethane can be obtained by dropping 1 μL of diiodomethane onto the scaffolding material and then similarly photographing the droplet image after 30 seconds.

The scaffolding material for stem cell culture preferably contains a synthetic resin from the viewpoint of suitably adjusting the dispersion component $\gamma^d$ and the dipole component $\gamma^p$ the surface free energy. In addition, the synthetic resin preferably contains at least any one of a polyvinyl acetal skeleton and poly(meth)acrylic ester skeleton from the viewpoint of suitably adjusting the dispersion component $\gamma^d$ and the dipole component $\gamma^p$ of the surface free energy.

FIG. 1 is a view summarizing the relationship between the dipole component $\gamma^p$ and the dispersion component $\gamma^d$ of the surface free energy of main synthetic resins. Each of FIGS. 2 and 3 is a partially enlarged view of FIG. 1.

The dispersion component $\gamma^d$ of the surface free energy of the scaffolding material for stem cell culture of the present invention is 24.5 or more and less than 45.0. The dispersion component $\gamma^d$ is more preferably 28.0 or more and 38.0 or less, still more preferably 32.8 or more and 36.0 or less.

The dipole component $\gamma^p$ of the surface free energy of the scaffolding material for stem cell culture of the present invention is 1.0 or more and less than 20.0. The dipole component $\gamma^p$ is more preferably 1.0 or more and 10.0 or less, still more preferably 2.5 or more and 5.0 or less.

The dispersion component $\gamma^d$ and the dipole component $\gamma^p$ can be controlled, for example, by appropriately changing the skeleton of the synthetic resin described below.

For example, the dispersion component $\gamma^d$ can be increased by increasing the amount of a non-polar functional group in the skeleton of the synthetic resin or by introducing a functional group having a cyclic structure, or can be decreased by reducing the amount of a butyl group component in the synthetic resin, or the like. The synthetic resin preferably contains at least any one of a polyvinyl acetal skeleton and a poly(meth)acrylic ester skeleton.

For example, the dipole component $\gamma^p$ can be increased by increasing the amount of a polar functional group in the skeleton of the synthetic resin or by introducing a functional group having an ether structure, or can be decreased by increasing the amount of a butyl group that is a non-polar functional group.

Synthetic Resin

The synthetic resin refers to a resin mainly composed of a polymer (hereinafter, also simply referred to as "polymer") obtained by polymerizing (including polycondensing) a polymerizable monomer (hereinafter, also simply referred to as "monomer"). The polymer also includes a copolymer of one or two or more polymerizable monomers.

Examples of the polymer include a polymer composed of one or more polymerizable monomers such as (un)saturated hydrocarbons, aromatic hydrocarbons, (un)saturated fatty acids, aromatic carboxylic acids, (un)saturated ketones, aromatic ketones, (un)saturated alcohols, aromatic alcohols, (un)saturated amines, aromatic amines, (un)saturated thiols, aromatic thiols and organosilicon compounds.

Specific examples of the polymer include polyolefin, polyether, polyvinyl alcohol, polyvinyl acetal, polyester, poly(meth)acrylic ester, epoxy resin, polyimide, polyimide, polyurethane, polycarbonate, cellulose and polypeptide. Among them, from the viewpoint of stem cell fixation, poly(meth)acrylic ester and polyvinyl acetal are preferable, and polyvinyl acetal is more preferable.

These polymers may be used alone or in combination of two or more. When two or more polymers are combined, they may be used as a mixture, or may be used as a polymer in which the skeletons of the two or more polymers are chemically bonded. When two or more polymers are combined as a synthetic resin, it is preferable to combine poly(meth)acrylic ester and polyvinyl acetal.

In the present specification, "(meth)acrylate" refers to at least one selected from the group consisting of (meth)acrylic ester and (meth)acrylic acid. In addition, poly(meth)acrylate is not only polymers obtained by polymerizing a monomer, (meth)acrylic ester or (meth)acrylic acid, but also includes those obtained by copolymerizing a monomer in addition to (meth)acrylic ester or (meth)acrylic acid.

The (meth)acrylic ester is not particularly limited, but includes alkyl (meth)acrylic esters, cyclic alkyl (meth) acrylic esters, aryl (meth)acrylic esters, (meth)acrylamides, polyethylene glycol (meth)acrylates and phosphorylcholine (meth)acrylates.

Examples of the alkyl (meth)acrylic ester include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth) acrylate, nonyl (meth)acrylate, isononyl (meth)acrylate, decyl (meth)acrylate, isodecyl (meth)acrylate, lauryl (meth) acrylate, stearyl (meth)acrylate and isotetradecyl (meth) acrylate.

These alkyl (meth)acrylic esters are not particularly limited, but may be substituted with various substituents including an alkoxy group having 1 to 3 carbon atoms and a tetrahydrofurfuryl group. Examples include methoxyethyl acrylate and tetrahydrofurfuryl acrylate.

Examples of the cyclic alkyl (meth)acrylic ester include cyclohexyl (meth)acrylate and isobornyl (meth)acrylate.

Examples of the aryl (meth)acrylic ester include phenyl (meth)acrylate and benzyl (meth)acrylate.

Examples of the acrylamide include (meth)acrylamide, N-isopropyl (meth)acrylamide, N-tert-butyl (meth)acrylamide, N,N'-dimethyl (meth)acrylamide, (3-(meth)acrylamidopropyl) trimethylammonium chloride, 4-(meth)acryloylmorpholine, 3-(meth)acryloyl-2-oxazolidinone, N-[3-(dimethylamino) propyl] (meth)acrylamide, N-(2-hydroxyethyl) (meth)acrylamide, N-methylol (meth) acrylamide and 6-(meth)acrylamidohexanoic acid.

Examples of the polyethylene glycol (meth)acrylate include methoxy-polyethylene glycol (meth)acrylate, ethoxy-polyethylene glycol (meth)acrylate, hydroxy-polyethylene glycol (meth)acrylate, methoxy-diethylene glycol (meth)acrylate, ethoxy-diethylene glycol (meth)acrylate, hydroxy-diethylene glycol (meth)acrylate, methoxy-triethylene glycol (meth)acrylate, ethoxy-triethylene glycol (meth)acrylate and hydroxy-triethylene glycol (meth)acrylate.

Examples of the phosphorylcholine (meth)acrylate include 2-(meth)acryloyloxyethyl phosphorylcholine.

Monomers other than the (meth)acrylic esters are not particularly limited, but include (meth)acrylic acids, ethylene and vinyl esters.

The (meth)acrylic esters may be used alone or in combination of two or more. In this specification, the (meth)acrylic acid is a generic term for acrylic acid and methacrylic acid, and the (meth)acrylate is a generic term for acrylate and methacrylate.

The first aspect of the present invention is preferably a combined one with the second aspect described below from the viewpoint of enhancing the fixation of stem cells.

Scaffolding Material for Stem Cell Culture 2

As a result of intensive studies, the present inventors have found that the above problems can be solved by using a synthetic resin containing a polyvinyl acetal resin, and thus have completed the present invention.

A second aspect of the present invention relates to a scaffolding material for stem cell culture containing a synthetic resin, wherein the synthetic resin contains a polyvinyl acetal resin, and the degree of acetalization of the polyvinyl acetal resin is higher than 60 mol %. The scaffolding material for stem cell culture of the present invention includes an aspect in which the material is composed of only a synthetic resin.

The scaffolding material for stem cell culture has so suitable hydrophilicity and strength that the fixation of stem cells after seeding is improved. In particular, in a serum-free medium culture containing no feeder cell or adhesive protein, the initial fixation rate of stem cells after seeding is improved.

Conventionally, it has not been reported to set the degree of acetalization of a synthetic resin higher than 60 mol % when the synthetic resin is used as a scaffolding material for stem cell culture. This is because there has been a concern about a decrease in the proportion of hydroxyl groups with an increase in the degree of acetalization, which decrease reduces the hydrophilicity of a resin, leading to a decreased fixation of stem cells after seeding to a scaffolding material for stem cell culture, or a decrease in permeability of polysaccharides necessary for cell culture and the like. However, the present inventors have found that strength is more important than hydrophilicity, and improving the strength of a scaffolding material for stem cell culture by setting the degree of acetalization to be higher than 60 mol % allows the fixation of stem cells after seeding to be improved, and thus have completed the present invention. Hereinafter, a detailed description is made of the polyvinyl acetal resin.

Polyvinyl Acetal Resin

The polyvinyl acetal resin is a resin synthesized by acetalizing polyvinyl alcohol with an aldehyde, which resin has an acetyl group, a hydroxyl group and an acetal group on the side chain.

The lower limit of the degree of acetalization of the polyvinyl acetal resin is preferably 60 mol %, and the upper limit thereof is preferably 90 mol %, When the degree of acetalization is 60 mol % or more, the fixation of stem cells is excellent, and thus cell proliferation can be performed with high efficiency. When the degree of acetalization is 90 mol % or less, the solubility in solvent can be better. The lower limit is more preferably 65 mol %, and the upper limit is more preferably 85 mol %.

The degree of acetal of the polyvinyl acetal resin can be measured by $^1$H-NMR measurement.

The aldehydes for use in acetalization include aldehydes having a chain aliphatic group, a cyclic aliphatic group or an aromatic group having 1 to 10 carbon atoms. As the aldehydes, conventionally publicly known aldehydes can be used.

The type of the aldehyde is not particularly limited, but includes formaldehyde, acetaldehyde, propionaldehyde, butyraldehyde, pentanal, hexanal, heptanal, octanal, nonanal, decanal, acrolein, benzaldehyde, cinnamaldehyde, perylaldehyde, formyipyridine, formylimidazole, formylpyrrole, formylpiperidine, formylpiperidine, formyitriazole, formyltetrazole, formylindole, formylisoindole, formylpurine, formylpurine, formylbenzimidazole, formylbenzotriazole, formylguinoline, formylisoquinoline, formylguinoxaline, formylcinnoline, formylpteridine, formylfuran, formyloxolane, formyloxane, formyithiophene, formylthiolane, formylthiane, formyladenine, formylguanine, formylcytosine, formylthymine and formyluracil. The aldehyde may be a chain or cyclic one.

The aldehyde is preferably formaldehyde, acetaldehyde, propionaldehyde, butyraldehyde or pentanal, more preferably butyraldehyde.

The lower limit of the degree of polymerization of the polyvinyl acetal resin is preferably 100, more preferably 200, still more preferably 500, even more preferably 1500. When the degree of polymerization is in the above range, the strength of the scaffolding material can be suitably maintained even when swelled in a medium to be used for cell culture, so that the cell proliferation is improved. The upper limit of the degree of polymerization is preferably 6000, more preferably 3000, still more preferably 2500. When the degree of polymerization is in the above range, the handleability is good and the scaffolding material can be suitably molded.

The polyvinyl alcohol may be a copolymer with a vinyl compound. The vinyl compound includes ethylene, allylamine, vinylpyrrolidone, maleic anhydride, maleimide, itaconic acid, (meth)acrylic acid, vinylamine and (meth)acrylic ester. As the (meth)acrylic ester, for example, the above-mentioned (meth)acrylic esters can be used.

The polyvinyl acetal resin may be a graft copolymer with a vinyl compound. The vinyl compound includes the above-mentioned compounds.

The graft copolymer contains a graft copolymer having a "unit composed of polyvinyl acetal" and a "unit composed of a vinyl compound" (hereinafter, also simply referred to as "graft copolymer"). The vinyl compound refers to a compound having a structural unit having an ethenyl group ($H_2C=CH-$).

In the present invention, the "unit composed of polyvinyl acetal" and the "unit composed of a vinyl compound" refer to "polyvinyl acetal" and a "unit composed of a vinyl compound" present in the graft copolymer. In addition, a graft copolymer having a unit composed of a unit composed of polyvinyl acetal and a unit composed of a vinyl compound refers to a branched copolymer in which, to a "unit composed of polyvinyl acetal" or a "unit composed of a vinyl compound" composing the main chain, a "unit composed of polyvinyl acetal" or a "unit composed of a vinyl compound" composing a side chain different from the main chain is bonded.

The molecular weight of the graft copolymer is not particularly limited, but it is preferable that the number average molecular weight (Mn) be 10,000 to 600,000, the weight average molecular weight (Mw) be 20,000 to 1,200,000 and the ratio (Mw/Mn) be 2.0 to 40. When the Mn, Mw and Mw/Mn are in such ranges, the strength of the scaffolding material for stem cell is suitably maintained.

Examples of the method for measuring the degree of acetalization in the graft copolymer include a method for measuring the degree of acetalization by $^1$H-NMR measurement in which a soluble component of the graft copolymer in xylene is dissolved in deuterated dimethyl sulfoxide.

The polyvinyl acetal resin preferably has on its part a Bronsted basic group or a Bronsted acidic group. In other words, a part of the polyvinyl acetal resin is preferably modified with a Bronsted basic group or a Bronsted acidic group, more preferably modified with a Bronsted basic group. When a part of the polyvinyl acetal resin is modified with a Bronsted basic group or a Bronsted acidic group, in serum-free medium culture containing no feeder cell or adhesive protein, the initial fixation rate after stem cell seeding is improved and the stem cell culture becomes easier.

In the present specification, a polyvinyl acetal resin having a Bronsted basic group or a Bronsted acidic group on a part of the polyvinyl acetal resin is referred to as a modified polyvinyl acetal resin.

The Bronsted basic group is a generic term for a functional group that can receive a hydrogen ion $H^+$ from another substance. Examples of the Bronsted basic group include amine-based basic groups such as a substituent having an amine structure, a substituent having an imine structure, a substituent having an amide structure and a substituent having an imide structure.

Accordingly, as such a polyvinyl acetal resin, polyvinyl acetal resins are preferable containing as a structural unit at least one selected from the group consisting of a structural unit having an amine structure, a structural unit having an imine structure, a structural unit having an amide structure and a structural unit having an imide structure. The total content of the structural unit having an amine structure, the structural unit having an imine structure, the structural unit having an amide structure and the structural unit having an imide structure is preferably 0.1 mol % to 30 mol % in the polyvinyl acetal resin, and more preferably 1 mol % to 10 mol % from the viewpoint of cell adhesion immediately after seeding.

In the present invention, the imine structure refers to a structure having a C=N bond. The polyvinyl acetal resin preferably has an imine structure on the side chain. In addition, the imine structure may be directly bonded to a carbon constituting the main chain of the polyvinyl acetal resin, or may be bonded via a linking group such as an alkylene group. Note that having the imine structure on the side chain includes having the imine structure on the graft chain of the polyvinyl acetal resin. Examples of the structural unit having an imine structure include structural unit represented by the following formula (1).

[Chemical 1]

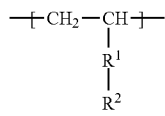

(1)

In the formula (1), $R^1$ represents a single bond or an alkylene group, and $R^2$ represents a group having an imine structure.

In the formula (1), when $R^1$ is an alkylene group, the preferred lower limit of the number of carbon atoms in the alkylene group is 1, and the preferred upper limit is 12. When the number of carbon atoms in the alkylene group exceeds 12, optimum strength may not be obtained. When $R^1$ is an alkylene group, the more preferred upper limit of the number of carbon atoms in the alkylene group is 5.

In the formula (1), when $R^1$ is an alkylene group, examples of the alkylene group includes linear alkylene groups such as a methylene group, ethylene group, trimethylene group, tetramethylene group, pentamethylene group, hexamethylene group, octamethylene group and decamethylene group, branched alkylene groups such as a methyl methylene group, methylethylene group, 1-methylpentylene group and 1,4-dimethylbutylene group, and cyclic alkylene groups such as a cyclopropylene group, cyclobutylene group and cyclohexylene group. Among them, a linear alkyl group such as a methylene group, ethylene group, trimethylene group and tetramethylene group is preferable, and a methylene group and ethylene group are more preferable.

The $R^2$ includes a functional group represented by the following formula (2).

[Chemical 2]

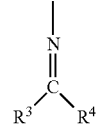

(2)

In the formula (2), $R^3$ represents a hydrogen atom or a hydrocarbon group having 1 to 18 carbon atoms, and $R^4$ represents a hydrocarbon group having 1 to 18 carbon atoms.

The hydrocarbon group includes a saturated hydrocarbon group, an unsaturated hydrocarbon group and an aromatic hydrocarbon group. The hydrocarbon group may be one composed of only any one of a saturated hydrocarbon group, an unsaturated hydrocarbon group and an aromatic hydrocarbon group, or one in which two or more of them are used.

Examples of the saturated hydrocarbon group include methyl, ethyl, n-propyl, isopropyl, n-butyl, iso-butyl, sec-butyl, tert-butyl, pentyl, hexyl, heptyl, 2-ethyl hexyl, octyl, nonyl, decyl, undecyl, dodecyl, tridecyl, tetradecyl, pentadecyl and octadecyl groups. Among them, a methyl group, ethyl group, n-propyl group and n-butyl group are preferable.

Examples of the aromatic hydrocarbon group include a phenyl group, toluyl group, xylyl group, t-butylphenyl group and benzyl group.

In the modified polyvinyl acetal resin, it is preferable that in the structural unit having an imine structure, $R^1$ be a single bond, $R^3$ be a hydrogen atom, a methyl group or an ethyl group, and R4 be a methyl group, an ethyl group or a propyl group.

In the polyvinyl acetal resin, the preferred lower limit of the content of the structural unit having an imine structure is 0.1 mol %, and the preferred upper limit is 20.0 mol %. When the content of the structural unit having an imine structure is 0.1 mol % or more, the viscosity stability over time becomes better. When the content of the structural unit having an imine structure is 20.0 mol % or less, acetalization can be sufficiently advanced. The more preferred lower limit of the content of the structural unit having an imine structure is 1.0 mol %, and the more preferred upper limit is 15.0 mol %.

The content of the structural unit having an imine structure can be measured by $^1$H-NMR measurement.

In the polyvinyl acetal resin, the ratio between the content of the structural unit having an imine structure and the degree of acetalization described below (the content of the structural unit having an imine structure/degree of acetalization) is preferably 0.001 to 0.5. Within the above range, high strength and excellent adhesiveness can be achieved at the same time, and the durability after adhesion can be improved.

The polyvinyl acetal resin preferably has a structural unit having an imino group (=NH) structure.

The polyvinyl acetal resin preferably has the imino group on the side chain. In addition, the imino group may be directly bonded to a carbon constituting the main chain of the polyvinyl acetal resin, or may be bonded via a linking group such as an alkylene group.

The modified polyvinyl acetal resin preferably has a structural unit having an amine structure or a structural unit having an amide structure.

The modified polyvinyl acetal resin preferably has the amine structure or the amide structure on the side chain. In addition, the amine structure or the amide structure may be directly bonded to a carbon constituting the main chain of the modified polyvinyl acetal resin, or may be bonded via a linking group such as an alkylene group. Furthermore, the amine structure may be a primary amine, a secondary amine, a tertiary amine or a quaternary amine. Among them, a primary amine is preferable from the viewpoint of enhancing the fixation of stem cells.

Note that having the amine structure or the amide structure of the side chain means having the amine structure or the amide structure on the graft chain of the modified polyvinyl acetal resin.

In particular, the amine structure as preferably —$NH_2$. In the present invention, the amide structure refers to a structure having —C(=O)—NH—. In particular, the structural unit having the amine structure preferably is a structure represented by the following formula (3). In addition, the structural unit having the amide structure preferably has structure represented by the following formula (4).

[Chemical 3]

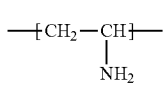

(3)

[Chemical 4]

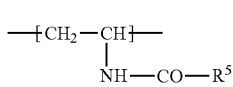

(4)

In the formula (4), $R^5$ represents a hydrogen atom or a hydrocarbon group having 1 to 10 carbon atoms. The hydrocarbon group includes an alkyl group, an alkenyl group, a cycloalkyl group and a cycloalkenyl group.

The preferred lower limit of the content of the structural unit having an amine structure or an amide structure is 0.1 mol %, and the preferred upper limit is 20 mol %. When the content of the structural unit having an amine structure or an amide structure is 0.1 mol % or mere, additional properties can be made sufficient. When the content is 20 mol % or less, the solubility is not so excessively increased that the modified polyvinyl acetal resin powder can be easily taken out by precipitation method. The more preferred lower limit of the content is 0.5 mol %, and the more preferred upper limit is 10 mol %. The content of the structural unit having an amine structure or an amide structure can be measured by $^1$H-NMR measurement. In addition, the preferred lower limit of the total content of the structural unit having an amine structure or an amide structure and the structural unit having an imine structure is 0.1 mol %, and the preferable upper limit is 20 mol %, The more preferred lower limit of the content is 0.5 mol %, and the more preferred upper limit is 10 mol %.

In the polyvinyl acetal resin, the ratio between the content of the structural unit having an imine structure and that of the structural unit having an amine structure or an amide structure (the structural unit having an imine structure/the structural unit having an amino group or an amide structure) is preferably 0.5/99.5 to 99.5/0.5. When the ratio is 0.5/99.5 or more, the viscosity stability over time can be sufficient, whereas when the above ratio is 99.5/0.5 or less, the crosslinking performance can be sufficiently exhibited from the viewpoint of improving the fixation of stem cells. The more preferred lower limit of the ratio is 5/95, and the more preferred upper limit is 90/10.

The Bronsted acidic group is a generic term for a functional group that can deliver a hydrogen ion $H^+$ to another substance.

The Bronsted acidic group includes a carboxyl group, a sulfonic acid group, a maleic acid group, a sulfinic acid group, a sulfenic acid group, a phosphoric acid group, a phosphonic acid group, and salts thereof. Among them, a carboxyl group is preferable as the Bronsted acidic group.

The method for modifying the polyvinyl acetal resin with the Bronsted acidic group is not particularly limited, but includes a method for copolymerizing the polyvinyl alcohol with the itaconic acid or (meth)acrylic acid and a method for introducing a Bronsted acidic group into the side chain of the polyvinyl alcohol.

The degree of acetalization of the polyvinyl acetal resin is not particularly limited, but the lower limit is preferably 60 mol %, and the upper limit is preferably 90 mol %. When the degree of acetalization is 60 mold or more, the fixation of stem cells is excellent, and thus cell proliferation can be performed with high efficiency. When the degree of acetalization is 90 mol % or less, the solubility in solvent can be better. The lower limit is more preferably 65 mol %, and the upper limit is more preferably 85 mol %. The degree of acetal of the polyvinyl acetal resin can be measured by $^1$H-NMR measurement.

The amount of the acetyl group in the polyvinyl acetal resin is not particularly limited, but the lower limit is preferably 0.0001 mol % and the upper limit is preferably 5 mol %.

Examples of the method for producing the polyvinyl acetal resin include a method for acetalizing using a conventionally known method a polyvinyl alcohol obtained by saponifying polyvinyl acetate obtained by copolymerizing the monomer having an imine structure with vinyl acetate. In addition, a method may also be used for introducing an imine structure by acetalizing using a conventionally known method a polyvinyl alcohol having a structural unit having an amino group or an amide structure. A method may also be used for acetalizing using a conventionally known method a modified polyvinyl alcohol having an imine structure obtained by post-modifying a polyvinyl alcohol having a structural unit having an amino group or an amide structure. Furthermore, an imine structure may be introduced by post-modifying an unmodified polyvinyl acetal resin. In other words, the modified polyvinyl acetal resin may be an acetalized product of a polyvinyl alcohol having a structural unit having an amino group or an amide structure. Among them, a method is preferable for producing a modified polyvinyl acetal resin having an imine structure by acetalizing a polyvinyl alcohol having a structural unit having an amino group or an amide structure. In particular, when such a method is used, an imine structure can be obtained by adding excessive amounts of aldehyde and acid catalyst for use in acetalization.

In the method for excessively adding aldehyde, it is preferable to add 70 to 150 parts by weight aldehyde to 100 parts by weight a polyvinyl alcohol having a structural unit having an amino group or an amide structure. Particularly, as the aldehyde, acetaldehyde, propionaldehyde, n-butyraldehyde, isobutyraidehyde, n-valeraldehyde and phenylaldehyde are preferable.

In the method for excessively adding an acid catalyst, it is preferable to add the acid catalyst in an amount of 0.5% by weight or more with respect to the whole weight. In addition, it is preferable to add 5.0 to 70.0 parts by weight acid catalyst to 100 parts by weight a polyvinyl alcohol having a structural unit having an amino group or an amide structure. Particularly, as the acid catalyst, hydrochloric acid, nitric acid, sulfuric acid and para-toluenesulfonic acid are preferable. In the case where such a method is used, examples of the method for confirming a structural unit having an amino group or an amide structure, or a structural unit having an imine structure include a confirming method by $^1$H-NMR.

The acetalization can be performed using a known method, and is preferably performed in an aqueous solvent, a mixed solvent of water and an organic solvent having compatibility with water, or an organic solvent. As the organic solvent compatible with water, for example, an alcohol-based organic solvent can be used Examples of the organic solvent include alcohol-based organic solvents, aromatic organic solvents, aliphatic ester-based solvents, ketone-based solvents, lower paraffin-based solvents, ether-based solvents and amine-based solvents. Examples of the alcohol-based organic solvent include methanol, ethanol, n-propanol, isopropanol, n-butanol and tert-butanol. Examples of the aromatic organic solvent include xylene, toluene, ethylbenzene and methyl benzoate.

Examples of the aliphatic ester-based solvent include methyl acetate, ethyl acetate, butyl acetate, methyl propionate, ethyl propionate, methyl butyrate, ethyl butyrate, methyl acetoacetate and ethyl acetoacetate.

Examples of the ketone-based solvent include acetone, methyl ethyl ketone, methyl isobutyl ketone, cyclohexanone, methylcyclohexanone, benzophenone and acetophenone. The lower paraffin-based solvents include hexane, pentane, octane, cyclohexane and decane. The ether-based solvents include diethyl ether, tetrahydrofuran, ethylene glycol dimethyl ether, ethylene glycol diethyl ether and propylene glycol diethyl ether. The amide-based solvents include N, N-dimethylformamide, N,N-dimethylacetamide, N-methylpyrrolidone and acetanilide.

The amine-based solvents include ammonia, trimethylamine, triethylamine, n-butylamine, di-n-butylamine, tri-n-butylamine, aniline, N-methylaniline, N,N-dimethylaniline and pyridine.

These can be used alone or as a mixture of two or more solvents. Among them, ethanol, n-propanol, isopropanol and tetrahydrofuran are particularly preferable from the viewpoints of solubility in a resin and simplicity during purification.

The acetalization is preferably performed in the presence of an acid catalyst. The acid catalyst is not particularly limited, but includes mineral acids such as sulfuric acid, hydrochloric acid, nitric acid and phosphoric acid, carboxylic acids such as formic acid, acetic acid and propionic acid, and sulfonic acids such as methanesulfonic acid, ethanesulfonic acid, benzenesulfonic acid and para-toluenesulfonic acid. These acid catalysts may be used alone or in combination of two or more compounds. Among them, hydrochloric acid, nitric acid and sulfuric acid are preferable, and hydrochloric acid is particularly preferable.

The scaffolding material for stem cell of the present invention allows for use as scaffolding materials for stem cells whose type is not particularly limited. Especially, the material is preferably used for culturing pluripotent stem cells, particularly iPS cells. In a serum-free medium culture containing no feeder cell or adhesive protein, the initial fixation rate of stem cells after seeding is improved, and stem cell culture can be suitably performed.

Stem Cell Culture Method

According to the scaffolding material for stem cell culture, although various stem cells can be cultured, in consideration of the properties, the scaffolding material is preferably used for culturing pluripotent stem cells among stem cells. This is because, although pluripotent stem cells are said to have a low fixation rate during culture after seeding in general, the scaffolding material for stem cell culture is hardly swelled with the moisture in a culture medium, and thus can maintain so suitable hydrophilicity and strength that the fixation rate of pluripotent stem cells after seeding is improved.

In stem cell culture, the scaffolding material for stem cell culture can be used not only for planar culture (two-dimensional culture method) but also for culturing stem cells on a base material in a state closer to an in-vivo state, such as a porous membrane or a hydrogel (three-dimensional culture method). This is because stem cells can be efficiently proliferated by using the scaffolding material for cell culture in a bioreactor or the like.

The scaffolding material for cell culture is preferably used in a two-dimensional culture method because it has suitable hydrophilicity and strength.

The container for planar culture (two-dimensional culture method) is not particularly limited for shape and size, but includes a test plate for cell culture having one or more wells (holes) and a flask for cell culture. The number of wells in the microplate is not limited, but includes, for example, 2, 4, 6, 12, 24, 48, 96 and 384. The shape of the well is not particularly limited, but includes, for example, a perfect circle, ellipse, triangle, square, rectangle, and pentagon. The shape of the bottom surface of the well is not particularly limited, but includes a flat bottom, a round bottom and irregularities.

The material of the test plate for cell culture having one or more wells (holes) or the material of the flask for cell culture are not particularly limited, but includes a polymer resin, metal and inorganic material. The polymer resin includes polystyrene, polyethylene, polypropylene, polycarbonate, polyester, polyisoprene, cycloolefin polymer, polyimide, polyamide, polyamideimide, (meth)acrylic res epoxy resin and silicone. The metal includes stainless steel, copper, iron, nickel, aluminum, titanium, gold, silver and platinum. The inorganic material includes silicon oxide (glass), aluminum oxide, titanium oxide, zirconium oxide, iron oxide and silicon nitride.

In addition to the above, the scaffolding material for cell culture can be used in a suspension culture method in which stem cells are freely suspended and grown in a medium.

Pluripotent Stem Cell Culture Method

In the pluripotent stem cell culture method, it is preferable to seed a cell mass on a scaffolding material for stem cell culture containing a synthetic resin.

The cell mass can be obtained by adding a cell detaching agent to confluent culture container and uniformly performing crushing by pipetting. The cell detaching agent is not particularly limited, but is preferably an ethylenediamine/phosphate buffer solution. The size of the cell mass is preferably 50 to 200 μm.

Other Embodiments

In addition to the scaffolding material for stem cell culture, the present invention provides an invention using the scaffolding material for stem cell culture as another embodiment.

For example, a carrier (medium) for stem cell culture containing the scaffolding material for stem cell culture and a polysaccharide is provided. Various polysaccharides can be used as the polysaccharide without any particular limitation. Among them, water-soluble polysaccharides are preferable.

A container for stem cell culture provided with a resin film on at least a part of a cell culture region is provided, wherein the scaffolding material for stem cell culture is used as the resin film. The container is not particularly limited as long as it has a resin film on at least a part of the cell culture region, but various containers can be used. As the container, the container for planar culture, a bioreactor or the like can be used.

In addition to the above, there is provided a fiber for stem cell culture including the scaffolding material for stem cell culture. In this case, it is preferable that the scaffolding material for stem cell culture be applied on the fiber. In addition, the scaffolding material for stem cell culture may be in a form impregnated or kneaded in the fiber. The fiber for stem cell culture is suitable for a three-dimensional culture method for stem cells that are difficult to adhere to a planar structure such as a flask, but easily adhere to a three-dimensional structure such as a fibril-like structure. The fiber is particularly suitable for culturing adipose stem cells among stem cells.

The scaffolding material for stem cell culture may be cross-linked. This is because crosslinking can suppress water swelling and suitably increase the strength. A crosslinking agent may be further added to the scaffolding material for stem cell culture to effect crosslinking.

The crosslinking agent is not particularly limited, but includes polyalcohol, polycarboxylic acid, hydroxycarboxylic acid, metal soap and polysaccharides.

The polyalcohol is not particularly limited, but includes ethylene glycol, propylene glycol, butanediol, pentanediol, hexanediol, heptanediol, octanediol, nonanediol, decanediol, dodecanediol, undecanediol, diethylene glycol, triethylene glycol, tetraethylene glycol, polyethylene glycol, catechol, pyrogallol, diboronic acid, methylenediboronic acid, ethylenediboronic acid, propylene diboronic acid, phenylenediboronic acid, biphenyldiboronic acid and bisphenol derivatives.

The polycarboxylic acid is not particularly limited, but includes oxalic acid, malonic acid, succinic acid, glutaric acid, adipic acid, pimelic acid, suberic acid, azelaic acid, sebacic acid, phthalic acid and poly(meth)acrylic acid.

The hydroxycarboxylic acid is not particularly limited, but includes glycolic acid, lactic acid, tartronic acid, glyceric acid, hydroxybutyric acid, malic acid, tartaric acid, cytomaric acid, citric acid, isocitric acid, leucic acid, mevalonic acid, pantoic acid, ricinoleic acid, ricineraidic acid, cerebronic acid, quinic acid, shikimic acid, hydroxybenzoic acid, salicylic acid, creosoteic acid, vanillic acid, syringic acid, pyrocatechuic acid, resorcylic acid, protocatechuic acid, gentisic acid, orsellinic acid, gallic acid, mandelic acid, benzilic acid, atrolactic acid, melilotic acid, phloretic acid, coumaric acid, umbellic acid, caffeic acid, ferulic acid, sinapinic acid and hydroxystearic acid.

The metal soap is not particularly limited, but includes salts of fatty acids such as stearic acid, lauric acid, ricinoleic acid and octylic acid with metals such as lithium, sodium, magnesium, calcium, barium, zinc and aluminum.

The polysaccharides are not particularly limited, but include pectin, guar gum, xanthan gum, tamarind gum, carrageenan, propylene glycol, carboxymethylcellulose, amylose, amylopectin, glycogen, cellulose, chitin, agarose, carrageenan, heparin, hyaluronic acid, xyloglucan and glucomannanic acid.

EXAMPLES

Hereinafter, description is made of the present invention with reference to Examples and Comparative Examples, but the present invention is not limited to the following Examples. The content of the structural unit, for example, structural unit having an amine structure (mol %), content of the structural unit having an imine structure (mol %), content of the structural unit having an amide structure (mol %), degree of acetalization (mol %), amount of acetyl group (mol %), amount of hydroxyl group (mol %) and amount of (meth)acrylic ester (mol %) in an obtained synthetic resin, modified polyvinyl acetal, resin were measured by dissolving the synthetic resin in DMSO-d6 (dimethyl sulfoxide) and using $^1$H-NMR (nuclear magnetic resonance spectrum).

Example 1

Preparation of Polyvinyl Butyral

A reactor equipped with a stirrer was charged with 2700 ml of ion-exchanged water, 300 g of polyvinyl alcohol having an average degree of polymerization of 250 and a degree of saponification of 99 mol %, followed by dissolution by heating with stirring to prepare a solution. Next, to the solution, 35% by weight hydrochloric acid as a catalyst was added such that the concentration of hydrochloric acid became 02% by weight, and after the temperature was adjusted to 15° C., 22 g of n-butyraldehyde (n-BA) was added while being stirred. Thereafter, when 148 g of n-butyraldehyde (n-BA) was added, polyvinyl butyral was precipitated in the form of white particles. Fifteen minutes after the precipitation, 35% by weight hydrochloric acid was added such that the concentration of hydrochloric acid became 1.8% by weight, followed by heating to 50° C. for aging at 50° C. for 2 hours. Next, the solution was cooled and neutralized, and then the polyvinyl butyral was washed with water and dried.

The obtained polyvinyl butyral had an average degree of polymerization of 250, an amount of hydroxyl group of 28 mol %, an amount of acetyl group of 1 mol % and a degree of acetalization of 71 mol %.

Preparation of Container for Cell Culture

By dissolving 1 q of the obtained polyvinyl butyral in 19 g of butanol, a solution of polyvinyl butyral was obtained. By discharging 150 μL of the obtained solution of polyvinyl butyral onto a φ22 mm cover glass (manufactured by Matsunami Glass Ind., Ltd., 22 round No. 1 was used after dust was removed with air duster) and spinning it at 2,000 rpm for 20 seconds using a spin coater, a smooth resin film was obtained. By placing the obtained resin film on a φ22 mm polystyrene dish together with the cover glass, a container for cell culture was obtained.

Surface Free Energy

The surface free energy of the resin film was measured using a contact angle meter (manufactured by Kyowa Interface Science, Inc., DMo-701). A contact angle of pure water was obtained by dropping 1 μL of pure water onto the resin film, and then photographing the droplet image after 30 seconds. In addition, a contact angle of diiodomethane was obtained by dropping 1 μL of diiodomethane onto the resin film, and then photographing the droplet image after 30 seconds. From the obtained contact angles, the surface free energy γ, dispersion component $γ^d$ and dipole component $γ^p$ were derived using Kaelble-Uy theory.

A test was performed on the container for cell culture provided with the resin film under the following conditions.

Method for Cell Culture Test

To the obtained container for cell culture, 1 mL of phosphate buffered saline was added, and the mixture was allowed to stand for 1 hour in an incubator at 37° C. After removing the phosphate buffered saline in the dish, $1.5 \times 10^4$ h-iPS cells 253G1 were seeded for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of medium, and adding 250 μL of new TeSR E8 such that the ROCK-Inhibitor (Y27632) was adjusted to be at 10 μM.

Method for Cell Mass Culture Test

To the obtained container for cell culture, 1 mL of phosphate buffered saline was added, and the mixture was allowed to stand for 1 hour in an incubator at 37° C. Thereafter, the phosphate buffered saline in the culture container was removed. A confluent colony of h-iPS cells 252G1 was added to a 35 mm dish, and then 1 mL of 0.5 mM ethylenediamine/phosphate buffer solution was added, followed by standing at room temperature for 2 minutes. Thereafter, the ethylenediamine/phosphate buffer solution was removed, $1.0 \times 10^5$ cell mass crushed to 50 to 200 μm by pipetting with 1 mL of TeSR E8 medium was seeded in the culture container for performing culture in the presence of 1 mL of medium TeSR E8 (manufactured by STEM CELL) and 10 μM of ROCK-Inhibitor (Y27632) in an incubator at 37° C. under a $CO_2$ concentration of 5%. Every 24 hours, the medium was exchanged by removing 750 μL of the medium and adding 250 μL of new TeSR E8.

Evaluation Method for Culture (1) Initial Adhesion

In the cell culture test, a cell image 24 hours after the cell seeding was obtained using a phase-contrast microscope (manufactured by Olympus Corporation, IX73) at a magnification of 10×10. At that time, an image of a visual field showing the most average form of adhesion in the culture container was obtained. The obtained images were compared with Samples 1 to 10 in FIG. 4 to evaluate the initial adhesion in consideration of the number of adherent cells and the morphology of adherent cells. In FIG. 4, it is shown that the number of cells increases from Samples 1 to 8 in this order. In addition, it is shown that the pseudopodia of the cells elongate and the cells are in a better adhesion state, from Samples 8 to 10 in this order. The obtained results are summarized in FIGS. 5 and 6.

(2) Cell Proliferation

In the cell culture test, a cell image 5 days after the cell seeding was obtained using a phase-contrast microscope (manufactured by Olympus Corporation, IX73) at a magnification of 10×4. At that time, an image of a visual field showing the most average form of adhesion in the culture container was obtained. The cell proliferation was evaluated by comparing the obtained image with Samples 1 to 10 in FIG. 7. In FIG. 7, a higher evaluation was obtained as the colony grew due to cell proliferation. When the colony grows too much in the lateral direction (the vertical and horizontal direction in the view), it starts to pile up in the vertical direction (the direction toward the front side of the view), so that light transmittance tends to decrease. The obtained results are summarized in FIGS. 8 and 9.

(3) Maintenance of Adhesion

In the cell mass culture test, the time during which the cell mass could maintain adhesion was evaluated according to the following criteria.

0: All cells were detached in less than 30 minutes after medium exchange.

1 Adhesion was maintained for 30 minutes or more after medium exchange, but all cells were detached in less than 1 hour.

2: Adhesion was maintained for 1 hour or more after medium exchange, but all cells detached in less than 24 hours.

3: Adhesion was maintained for 24 hours or more after medium exchange.

The obtained cell mass was confirmed to maintain undifferentiation by alkaline phosphatase (ALP) staining test.

Example 2

The test was performed in the same manner as in Example 1 except that polyvinyl alcohol having an average degree of polymerization of 850 and a degree of saponification of 99 mol % was used.

Example 3

The test was performed in the same manner as in Example 1 except that polyvinyl alcohol having an average degree of polymerization of 1,700 and a degree of saponification of 99 mol % was used.

Example 4

The test was performed in the same manner as in Example 1 except that polyvinyl alcohol having an average degree of polymerization of 2,400 and a degree of saponification of 99 mol % was used, and that acetaldehyde was used instead of n-butyraldehyde (n-BA).

Example 5

The test was performed in the same manner as in Example 1 except that polyvinyl alcohol having an average degree of polymerization of 850, a degree of saponification of 98 mold, and a degree of ethylene modification of 4 mol % was used.

Example 6

The test was performed in the same manner as in Example 1 except that polyvinyl alcohol having an average degree of polymerization of 250 and a degree of saponification of 99 mol %, and containing 2 mol % structural unit having an amino group represented by the formula (3) was used.

Example 7

The test was performed in the same manner as in Example 1 except that polyvinyl alcohol having an average degree of polymerization of 1,600 and a degree of saponification of 99 mol %, and containing 2 mol % structural unit having an amino group represented by the formula (3) was used.

Example 8

In 500 parts by weight tetrahydrofuran, 100 parts by weight polyvinyl acetal having a degree of polymerization of about 250 obtained in Example 1 and 1 part by weight N-vinylpyrrolidone were dissolved to prepare a graft copolymer resin solution. In the prepared resin solution, 0.05 parts by weight Irgacure184 (manufactured by BASF) was dissolved, and the resultant mixture was applied onto a PET film. The coated product was irradiated with light having a wavelength of 365 nm at an integrated light amount of 2000 mJ/cm$^2$ using a UV conveyor device "ECS301G1" manufactured by Eye Graphics Co., Ltd. at 25° C. to prepare a composite resin solution. The prepared composite resin solution was vacuum-dried at 80° C. for 3 hour, to prepare a composite resin. The prepared resin was measured for weight average molecular weight in terms of polystyrene by GPC method using "2690 Separations Model" manufactured by Waters Corporation as a column. The weight average molecular weight was about 40,000. The prepared composite resin was adjusted to a 3% by weight butanol solution, and the test was conducted in the same manner as in Example 1.

Example 9

The test was performed in the same manner as in Example 8 except that 10 parts by weight N-vinylpyrrolidone was added to 100 parts by weight polyvinyl acetal. The weight average molecular weight of the obtained resin was about 60,000.

Example 10

The test was performed in the same manner as in Example 8 except that 30 parts by weight N-vinylpyrrolidone was added to 100 parts by weight polyvinyl acetal. The weight average molecular weight of the obtained resin was about 50,000.

Example 11

The test was performed in the same manner as in Example 8 except that 5 parts by weight tetrahydrofurfuryl acrylate was added to 100 parts by weight polyvinyl acetal. The weight average molecular weight of the obtained resin was about 60,000.

Example 12

The test was performed in the same manner as in Example 8 except that 5 parts by weight methoxyethyl acrylate was added to 100 parts by weight polyvinyl acetal. The weight average molecular weight of the obtained resin was about 70,000.

Example 13

The test was performed in the same manner as an Example 8 except that 5 parts by weight butyl methacrylate was added to 100 parts by weight polyvinyl acetal. The weight average molecular weight of the obtained resin was about 60,000.

Example 14

In 300 parts by weight tetrahydrofuran, 75 parts by weight N-isopropylacrylamide and 25 parts by weight butyl methacrylate were dissolved to prepare an acrylic monomer solution. In the prepared acrylic monomer solution, 2 parts by weight Irgacure184 (manufactured by BASF) was dissolved, and the resultant mixture was applied onto a TET fill. The coated product was irradiated with light having a wavelength of 365 nm at an integrated light amount of 2,000 mJ/cm$^2$ using a UV conveyor device "ECS301G1" manufactured by Eye Graphics Co., Ltd. at 25° C. to prepare an acrylic resin solution. The prepared acrylic resin solution was vacuum-dried at 80° C. for 3 hours to prepare an acrylic resin. The prepared acrylic resin was adjusted to a 3% by weight butanol solution, and the test was conducted in the same manner as in Example 1. The weight average molecular weight of the obtained acrylic resin was about 100,000.

Example 15

An acrylic resin was obtained in the same manner as in Example 14 except that 90 parts by weight methoxyethyl acrylate and 10 parts by weight butyl methacrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained acrylic resin was about 80,000.

Example 16

An acrylic resin was obtained in the same manner as in Example 14 except that 75 parts by weight methoxyethyl acrylate and 25 parts by weight butyl methacrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained resin was about 90,000.

Example 17

An acrylic resin was obtained in the same manner as in Example 14 except that 2 parts by weight butyl methacrylate and 98 parts by weight ethyl acrylate were used, instead of 75 parts by weight N-isopropylacrylamide and 25 parts by weight butyl methacrylate. The prepared acrylic resin was adjusted to a 3% by weight butanol solution, and the test was conducted in the same manner as in Example 1. The weight average molecular weight of the obtained acrylic resin was about 80,000.

Comparative Example 1

The test was performed in the same manner as in Example 1 using only a polystyrene dish without using the scaffolding material.

Comparative Example 2

The test was performed in the same manner as in Example 1 except that the amount of the second addition of n-butyraldehyde (n-BA) was changed from 148 g to 89 g.

Comparative Example 3

The test was performed in the same manner as in Example 1 except that polyvinyl alcohol having an average degree of polymerization of 1000 and a degree of saponification of 98 mol % was used as the synthetic resin.

Comparative Example 4

A polyacrylamide resin was obtained by mixing 100 parts by weight N-isopropylacrylamide, 75 parts by weight ethyl acetate and 0.5 parts by weight azobisisobutyronitrile, followed by polymerization at 65° C. for 8 hours under a nitrogen atmosphere. The prepared resin was measured for weight average molecular weight in terms of polystyrene by GPC method using "2690 Separations Model" manufactured by Waters Corporation as a column. The weight average molecular weight was about 90,000 (the degree of polymerization was about 800). Other operations in the test were performed in the same manner as in Example 1.

Comparative Example 5

The test was performed in the same manner as in Comparative Example 4 except that 100 parts by weight ethyl acrylate was used instead of 100 parts by weight N-isopropylacrylamide.

Comparative Example 6

The test was performed in the same manner as in Comparative Example 4 except that 100 parts by weight butyl methacrylate was used instead of 100 parts by weight N-isopropylacrylamide. The weight average molecular weight of the obtained resin was about 90,000.

Comparative Example 7

The test was performed in the same manner as in Example 8 except that 70 parts by weight N-vinylpyrrolidone was added to 30 parts by weight polyvinyl acetal. The weight average molecular weight of the obtained resin was about 90,000.

The obtained results are summarized in Tables 1 and 2. FIGS. 5 and 6 show phase contrast micrographs of the cells 24 hours after seeding. FIGS. 8 and 9 show phase contrast micrographs of the cells 5 days after seeding. No differentiated cells were observed in any of the Examples and Comparative Examples.

TABLE 1

| | | | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Synthetic resin | Polyvinyl acetal resin | Degree of acetalization (mol %) | 71 | 68 | 65 | 66 | 64 | 77 | 76 | 70 | 65 | 54 |
| | | Amount of acetyl group (mol %) | 1 | 1 | 1 | 1 | 2 | 1 | 1 | 1 | 1 | 1 |
| | | Amount of hydroxyl group (mol %) | 28 | 31 | 34 | 33 | 30 | 20 | 21 | 28 | 25 | 21 |
| | | Content of structural unit having amine group (1) (mol %) | — | — | — | — | — | 0.3 | 0.3 | — | — | — |
| | | Content of structural unit having imine structure (2) (mol %) | — | — | — | — | — | 1.7 | 1.7 | — | — | — |
| | | Content of structural unit having amide structure (3) (mol %) | — | — | — | — | — | — | — | 1 | 9 | 24 |
| | | Total content of structural unit having amine structure, structural unit having imine group and structural unit having amide structure ((1) + (2) + (3)) (mol %) | — | — | — | — | — | 2.0 | 2.0 | 1 | 9 | 24 |
| | | Degree of polymerization | 250 | 850 | 1700 | 2400 | 850 | 250 | 1600 | 250 | 250 | 250 |
| | Surface free energy | $\gamma^d$ | 32.5 | 32.6 | 33.5 | 31.3 | 34.2 | 34.2 | 34.8 | 33.0 | 35.7 | 36.2 |
| | | $\gamma^p$ | 3.5 | 3.7 | 3.5 | 4.6 | 3.3 | 3.3 | 3.6 | 3.2 | 2.6 | 2.2 |
| Evaluation for culture | Initial adhesion | | 5 | 5 | 6 | 6 | 6 | 8 | 8 | 9 | 9 | 7 |
| | Cell proliferation | | 4 | 5 | 6 | 6 | 5 | 6 | 7 | 9 | 9 | 6 |
| | Maintenance of adhesion | | 1 | 1 | 1 | 1 | 1 | 2 | 2 | 3 | 3 | 2 |

TABLE 2

|  |  |  | Example 11 | Example 12 | Example 13 | Example 14 | Example 15 | Example 16 | Example 17 | Comparative Example 1 |
|---|---|---|---|---|---|---|---|---|---|---|
| Synthetic resin | Polyvinyl acetal resin | Degree of acetalization (mol %) | 68 | 68 | 68 | — | — | — | — | — |
|  |  | Amount of acetyl group (mol %) | 1 | 1 | 1 | — | — | — | — | — |
|  |  | Amount of hydroxyl group (mol %) | 27 | 27 | 27 | — | — | — | — | — |
|  |  | Content of structural unit having amine group (1) (mol %) | — | — | — | — | — | — | — | — |
|  |  | Content of structural unit having imine structure (2) (mol %) | — | — | — | — | — | — | — | — |
|  |  | Content of structural unit having amide structure (3) (mol %) | — | — | — | — | — | — | — | — |
|  |  | Tetrahydrofurfuryl acrylate unit (mol %) | 4 | — | — | — | — | — | — | — |
|  |  | Methoxyethyl acrylate unit (mol %) | — | 4 | — | — | — | — | — | — |
|  |  | Butyl methacrylate unit (mol %) | — | — | 4 | — | — | — | — | — |
|  |  | Total content of structural unit having amine structure, structural unit having imine group and structural unit having amide structure ((1) + (2) + (3)) (mol %) | — | — | — | — | — | — | — | — |
|  |  | Degree of polymerization | 250 | 250 | 250 | — | — | — | — | — |
|  | Poly(meth)acrylic ester | Content of structural unit having amide structure (mol %) | — | — | — | — | — | — | — | — |
|  |  | Butyl methacrylate unit (mol %) | — | — | — | — | — | — | — | — |
|  |  | Methoxyethyl acrylate unit (mol %) | — | — | — | — | — | — | — | — |
|  |  | Ethyl acrylate unit (mol %) | — | — | — | — | — | — | — | — |
|  |  | Degree of polymerization | — | — | — | 250 | 250 | 250 | 250 | — |
|  | Surface free energy | $\gamma^d$ | 35.1 | 34 | 34.4 | 24.8 | 38.9 | 42.9 | 42.7 | 45.8 |
|  |  | $\gamma^p$ | 2.9 | 4.2 | 2.4 | 9.2 | 17.9 | 8.6 | 5.8 | 5.8 |
| Evaluation for culture | Initial adhesion |  | 7 | 8 | 8 | 4 | 4 | 4 | 4 | 3 |
|  | Cell proliferation |  | 8 | 8 | 8 | 3 | 3 | 3 | 3 | 1 |
|  | Maintenance of adhesion |  | 2 | 2 | 2 | 1 | 1 | 1 | 1 | 0 |

|  |  |  | Comparative Example 2 | Comparative Example 3 | Comparative Example 4 | Comparative Example 5 | Comparative Example 6 | Comparative Example 7 |
|---|---|---|---|---|---|---|---|---|
| Synthetic resin | Polyvinyl acetal resin | Degree of acetalization (mol %) | 40 | 0 | — | — | — | 21 |
|  |  | Amount of acetyl group (mol %) | 3 | 2 | — | — | — | 0 |
|  |  | Amount of hydroxyl group (mol %) | 57 | 98 | — | — | — | 8 |
|  |  | Content of structural unit having amine group (1) (mol %) | — | — | — | — | — | — |
|  |  | Content of structural unit having imine structure (2) (mol %) | — | — | — | — | — | — |
|  |  | Content of structural unit having amide structure (3) (mol %) | — | — | — | — | — | 71 |
|  |  | Tetrahydrofurfuryl acrylate unit (mol %) | — | — | — | — | — | — |
|  |  | Methoxyethyl acrylate unit (mol %) | — | — | — | — | — | — |
|  |  | Butyl methacrylate unit (mol %) | — | — | — | — | — | — |
|  |  | Total content of structural unit having | — | — | — | — | — | 71 |

TABLE 2-continued

| | | | | | | | |
|---|---|---|---|---|---|---|---|
| | | amine structure, structural unit having imine group and structural unit having amide structure ((1) + (2) + (3)) (mol %) | | | | | | |
| | | Degree of polymerization | 250 | 1000 | — | — | — | 250 |
| | Poly(meth)acrylic ester | Content of structural unit having amide structure (mol %) | — | — | 100 | — | — | — |
| | | Butyl methacrylate unit (mol %) | — | — | — | — | 100 | — |
| | | Methoxyethyl acrylate unit (mol %) | — | — | — | — | — | — |
| | | Ethyl acrylate unit (mol %) | — | — | — | 100 | — | — |
| | | Degree of polymerization | — | — | 800 | 600 | 550 | 250 |
| | Surface free energy | $\gamma^d$ | 28.9 | 26.7 | 24.0 | 23.1 | 45.7 | — |
| | | $\gamma^p$ | 26.8 | 34.9 | 19.6 | 8.0 | 1.0 | — |
| Evaluation for culture | Initial adhesion | | 4 | 3 | 2 | 2 | 4 | 2 |
| | Cell proliferation | | 2 | 1 | 1 | 1 | 1 | 1 |
| | Maintenance of adhesion | | 0 | 0 | 0 | 0 | 0 | 0 |

The invention claimed is:

1. A scaffolding material for culturing a cell, having a dispersion component $\gamma^d$ of surface free energy of 24.5 mJ/m$^2$ or more and less than 45.0 mJ/m$^2$, and a dipole component $\gamma^p$ of surface free energy of 1.0 mJ/m$^2$ or more and less than 20.0 mJ/m$^2$, wherein the scaffolding material comprises a polyvinyl acetal resin, and the polyvinyl acetal resin is a graft copolymer with a vinyl compound.

2. The scaffolding material for culturing a cell according to claim 1, wherein the vinyl compound includes ethylene, allylamine, vinylpyrrolidone, maleic anhydride, maleimide, itaconic acid, (meth)acrylic acid, vinylamine, (meth)acrylic ester or any combination thereof.

3. The scaffolding material for culturing a cell according to claim 1, wherein the scaffolding material has the dispersion component $\gamma^d$ of surface free energy of 28.0 mJ/m$^2$ or more and 38.0 mJ/m$^2$ or less, and the dipole component $\gamma^p$ of surface free energy of 1.0 mJ/m$^2$ or more and 10.0 mJ/m$^2$ or less.

4. The scaffolding material for culturing a cell according to claim 1, wherein the scaffolding material is in the form of a resin film.

5. The scaffolding material for culturing a cell according to claim 1, wherein the polyvinyl acetal resin is a polyvinyl butyral resin.

6. The scaffolding material for culturing a cell according to claim 5, wherein the polyvinyl acetal resin contains as a structural unit at least one selected from the group consisting of a structural unit having an amine structure, a structural unit having an imine structure and a structural unit having an amide structure, and wherein the polyvinyl acetal resin has a total content of the structural unit having an amine structure, the structural unit having an imine structure and the structural unit having an amide structure of 0.1 mol % or more and 30 mol % or less.

7. The scaffolding material for culturing a cell according to claim 1, wherein a degree of acetalization of the polyvinyl acetal resin is higher than 60 mol %.

8. The scaffolding material for culturing a stem cell according to claim 7, wherein the polyvinyl acetal resin contains as a structural unit at least one selected from the group consisting of a structural unit having an amine structure, a structural unit having an imine structure and a structural unit having an amide structure.

9. The scaffolding material for culturing a stem cell according to claim 8, wherein the polyvinyl acetal resin has a total content of the structural unit having an amine structure, the structural unit having an imine structure and the structural unit having an amide structure of 0.1 mol % or more and 30 mol % or less.

10. The scaffolding material for culturing a stem cell according to claim 7, wherein the stem cell is a pluripotent stem cell.

11. The scaffolding material for culturing a cell according to claim 1, wherein the polyvinyl acetal resin contains as a structural unit at least one selected from the group consisting of a structural unit having an amine structure, a structural unit having an imine structure and a structural unit having an amide structure.

12. The scaffolding material for culturing a cell according to claim 11, wherein the polyvinyl acetal resin has a total content of the structural unit having an amine structure, the structural unit having an imine structure and the structural unit having an amide structure of 0.1 mol % or more and 30 mol % or less.

13. A container for culturing a cell, comprising a cell culture region and the scaffolding material for culturing a cell according to claim 1 on at least a part of the cell culture region.

14. A container for culturing a stem cell, comprising the scaffolding material for culturing a stem cell according to claim 7 on at least a part of a cell culture region.

15. A fiber for culturing a stem cell, comprising the scaffolding material for culturing a stem cell according to claim 7.

16. A method for culturing a cell, the method comprising culturing the cell on the scaffolding material according to claim 1.

17. The method for culturing a cell according to claim 16, comprising a step of seeding a cell mass on the scaffolding material for culturing a cell.

18. A method for culturing a stem cell, the method comprising culturing the stem cell on the scaffolding material according to claim 7.

19. The method for culturing a stem cell according to claim 18, comprising a step of seeding a cell mass on the scaffolding material for culturing a stem cell.

* * * * *